(12) United States Patent
Lin et al.

(10) Patent No.: US 11,326,164 B2
(45) Date of Patent: May 10, 2022

(54) TRIMETHYLGLYCYLGLYCERIN COMPOSITIONS AND THEIR USE IN DEVELOPING ANTI-CANCER DRUGS AND RNA VACCINES

(71) Applicants: WJWU & LYNN Institute for Stem Cell Research, Santa Fe Springs, CA (US); Mello Biotech Taiwan Co., Ltd., Taipei (TW)

(72) Inventors: Shi-Lung Lin, Arcadia, CA (US); Samantha Chang-Lin, Arcadia, CA (US); Chin-Tsyh Donald Chang, Cerritos, CA (US)

(*) Notice: Subject to any disclaimer, the term of this patent is extended or adjusted under 35 U.S.C. 154(b) by 0 days.

(21) Appl. No.: 16/825,131

(22) Filed: Mar. 20, 2020

(65) Prior Publication Data

US 2021/0095280 A1    Apr. 1, 2021

Related U.S. Application Data

(60) Provisional application No. 62/907,666, filed on Sep. 29, 2019, provisional application No. 62/936,684, filed on Nov. 18, 2019, provisional application No. 62/949,943, filed on Dec. 18, 2019.

(51) Int. Cl.

| | |
|---|---|
| *A61K 47/00* | (2006.01) |
| *A61K 47/50* | (2017.01) |
| *A61K 47/51* | (2017.01) |
| *C12N 15/113* | (2010.01) |
| *A61K 39/39* | (2006.01) |
| *A61K 39/29* | (2006.01) |
| *A61K 39/215* | (2006.01) |
| *A61P 35/00* | (2006.01) |
| *A61K 39/21* | (2006.01) |
| *A61K 39/12* | (2006.01) |
| *A61K 39/145* | (2006.01) |

(52) U.S. Cl.
CPC ............ *C12N 15/113* (2013.01); *A61K 39/12* (2013.01); *A61K 39/145* (2013.01); *A61K 39/21* (2013.01); *A61K 39/215* (2013.01); *A61K 39/29* (2013.01); *A61K 39/292* (2013.01); *A61K 39/39* (2013.01); *A61P 35/00* (2018.01)

(58) Field of Classification Search
None
See application file for complete search history.

(56) References Cited

U.S. PATENT DOCUMENTS

| | | |
|---|---|---|
| 2006/0153804 A1 | 7/2006 | Lively et al. |
| 2014/0350085 A1 | 11/2014 | Lin et al. |
| 2015/0080454 A1 | 3/2015 | Kataoka et al. |

FOREIGN PATENT DOCUMENTS

| | | | |
|---|---|---|---|
| WO | WO 2015/099839 A1 | 7/2015 | |
| WO | WO-2015099839 A1 * | 7/2015 | ............. A61K 47/26 |

OTHER PUBLICATIONS

Schwinefus et al. Human Telomerase RNA Pseudoknot and Hairpin Thermal Stability with Glycine Betaine and Urea: Preferential Interactions with RNA Secondary and Tertiary Structures. Biochemistry 2007, 46, 9068-9079.*

English translation of the Written Opinion of the International Searching Authority, and International Search Report, dated Jun. 26, 2020, for International Application No. PCT/US20/23963.

* cited by examiner

*Primary Examiner* — Nianxiang Zou
(74) *Attorney, Agent, or Firm* — Birch, Stewart, Kolasch & Birch, LLP

(57) ABSTRACT

This invention generally relates to a group of novel chemical compositions and their use for formulating RNA- and/or DNA-based medicine drugs/vaccines into stable compound complexes useful for both in-vitro and in-vivo delivery. Particularly, the present invention teaches the synthesis of a group of novel trimethylglycyl chemicals and their use for formulating cosmetic, therapeutic- and/or pharmaceutical-grade nucleic acid compositions, including but not limited microRNA precursors (pre-miRNA/miRNA), small hairpin RNAs (shRNA), short interfering RNAs (siRNA), ribozymes, antisense oligonucleotides, RNA-DNA hybrids and DNA-based vectors/vaccines, with or without modification, into delivery complexes, which can then be absorbed by cells in vivo, ex vivo and/or in vitro through an active mechanism of endocytosis via acetylcoline receptors for releasing the therapeutic and pharmaceutical effects of the formulated nucleic acid compositions.

23 Claims, 19 Drawing Sheets

Specification includes a Sequence Listing.

FIG.3
glycerol (glycerin) 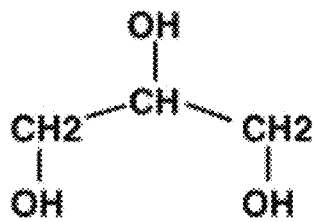 + trimethylglycine (TMG) 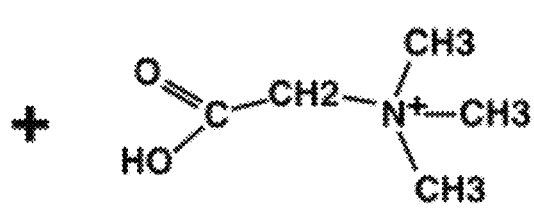
≥75°C, ≥100kPa
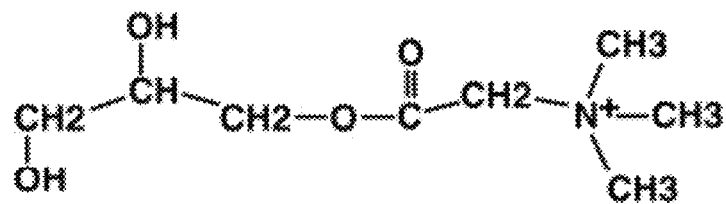
1- or 3-mono-trimethyl-glycylglycerin (1- or 3-TMGG)
or
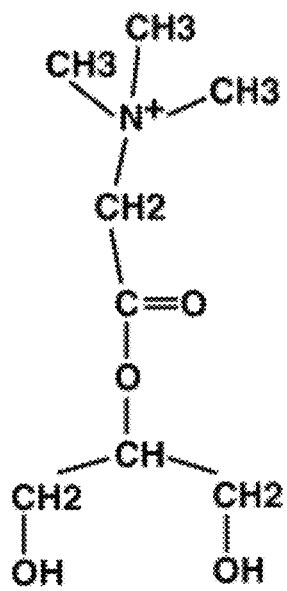
2-mono-trimethyl-glycylglycerin (2-TMGG)

FIG.4
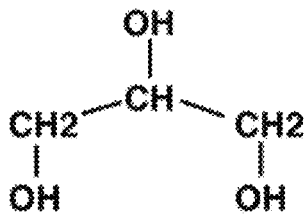
glycerol (glycerin)
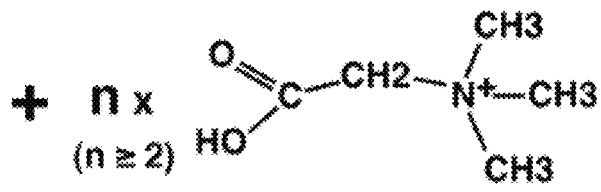
trimethylglycine (TMG)
+ n x
(n ≥ 2)
↓ ≥75°C, ≥100kPa ↓
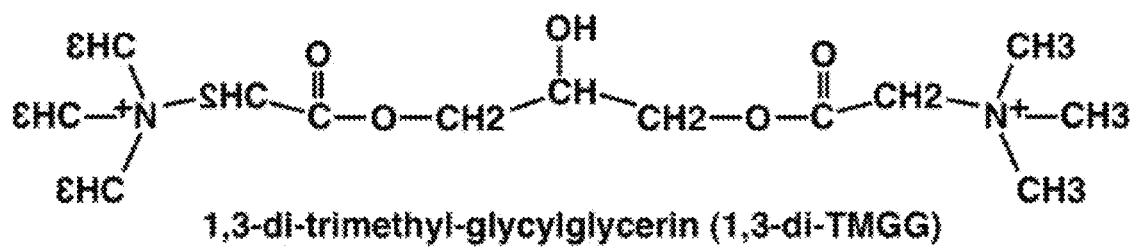
1,3-di-trimethyl-glycylglycerin (1,3-di-TMGG)
*or*
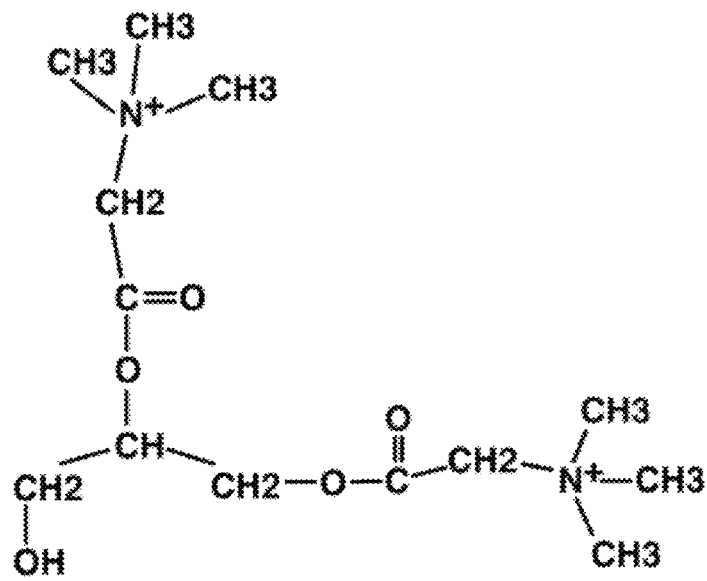
1,2- or 2,3-di-trimethyl-glycylglycerin
(1,2- or 2,3-di -TMGG)

FIG.6
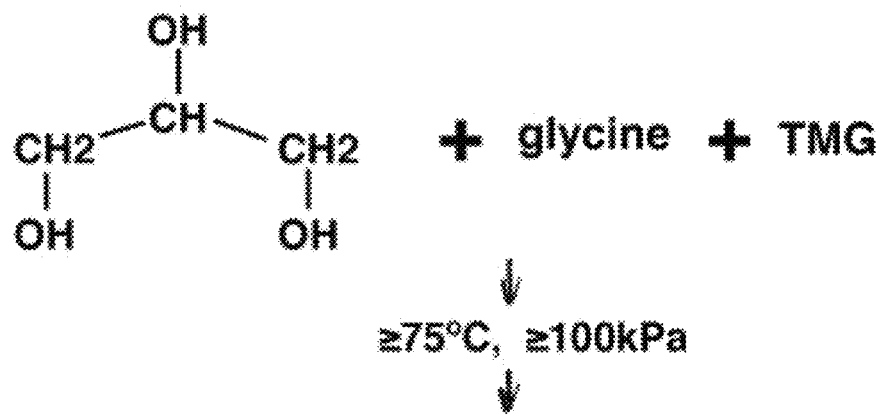
glycerol (glycerin) + glycine + TMG
≥75°C, ≥100kPa
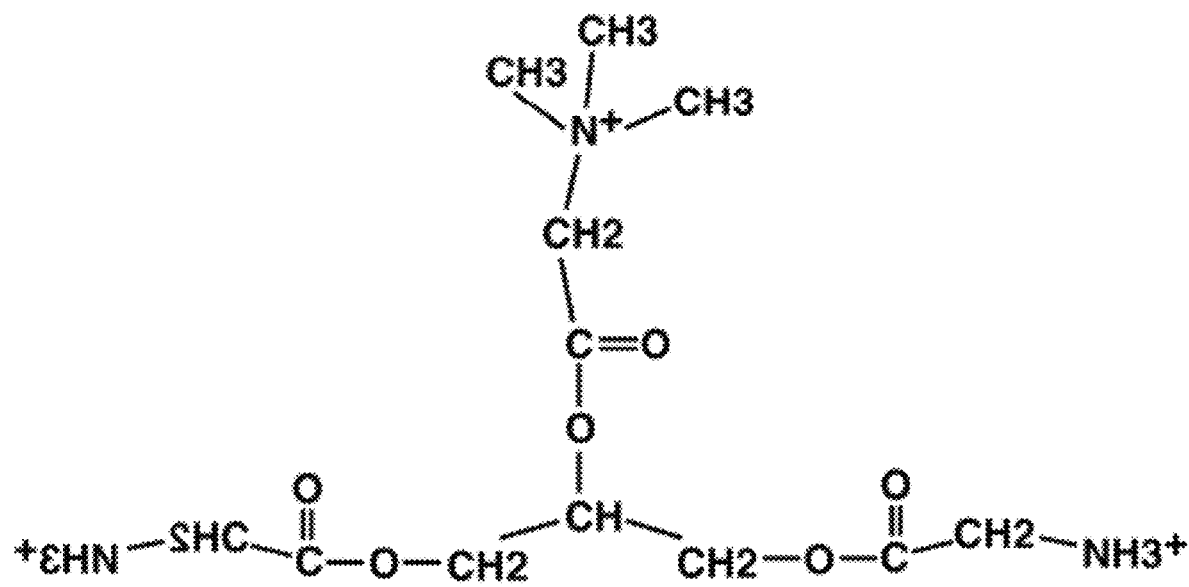
2-trimethylglycyl-1,3-di-glycylglycerin
(2-TMG-1,3-DGG)

FIG.7
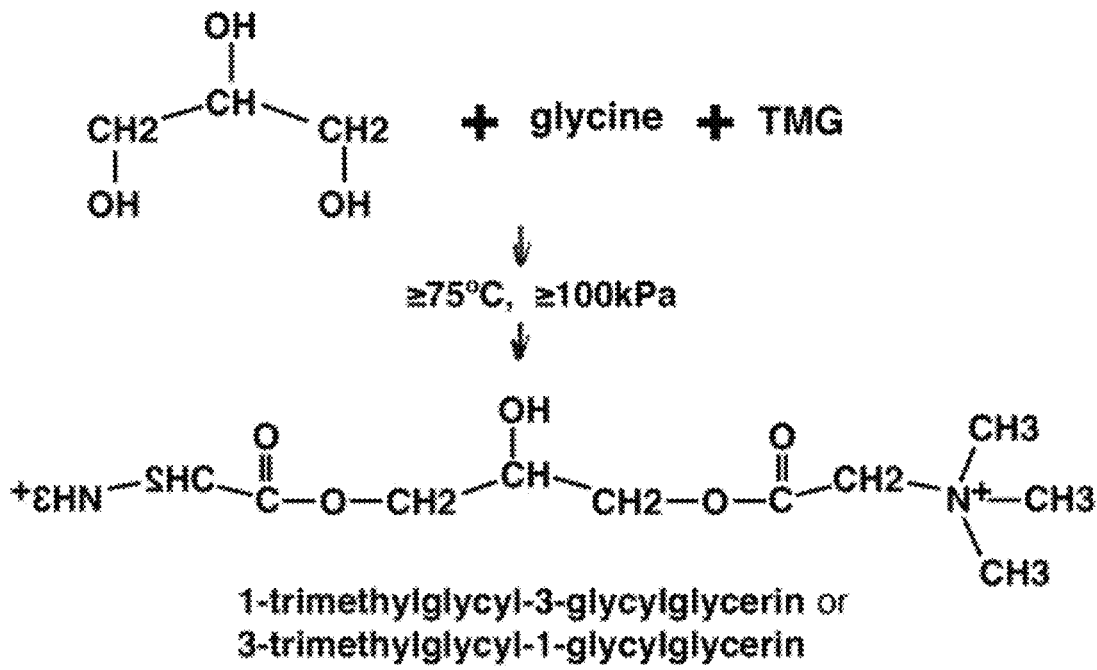
1-trimethylglycyl-3-glycylglycerin or
3-trimethylglycyl-1-glycylglycerin
or
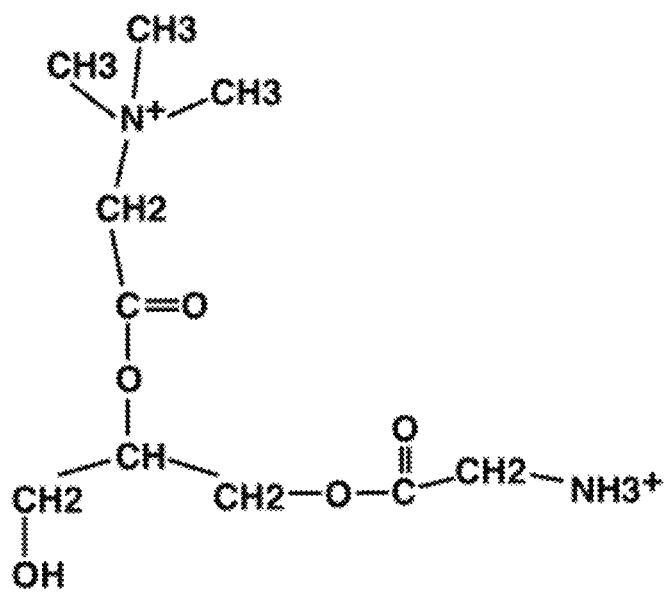
2-trimethylglycyl-1- or 3-glycylglycerin or
1- or 3-trimethylglycyl-2-glycylglycerin

FIG.10
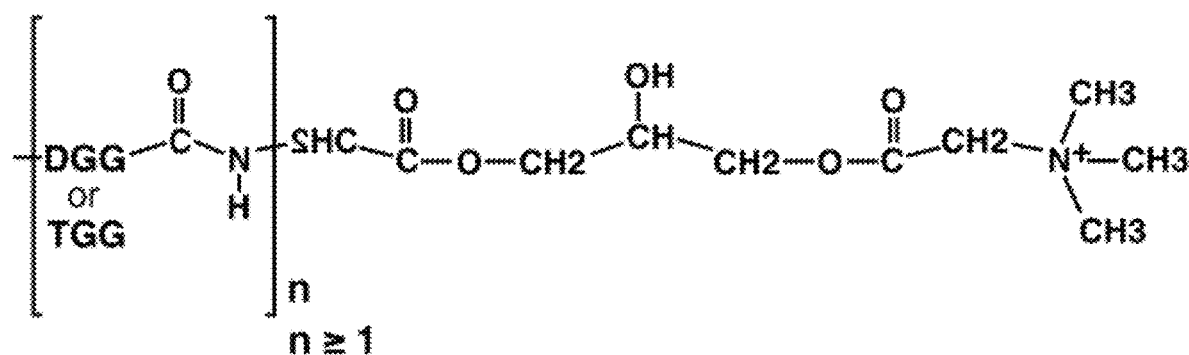
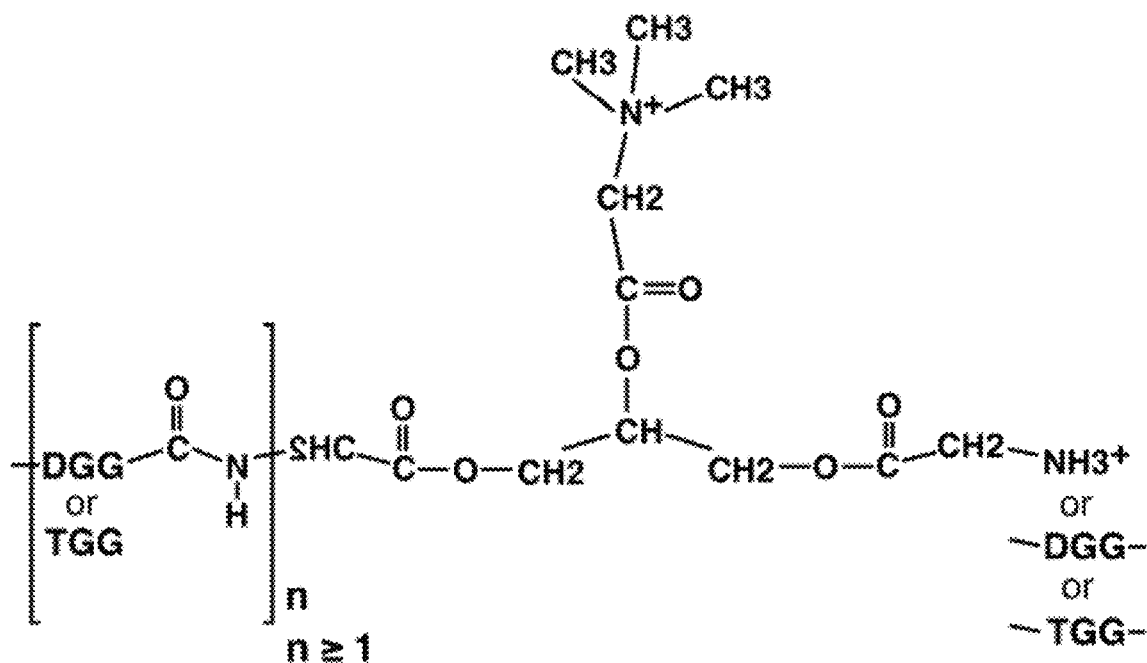
TMGG-DGG/TGG polymers

FIG.15

| | EGFR | p53 | K-ras | Colony formation ability | Effects on growth | Effects on colony formation |
|---|---|---|---|---|---|---|
| PC9/IR | del19 | R248Q | WT | | N.D. | sensitive |
| H1650 | del19 | WT | A183T | | N.D. | sensitive |
| CL1-0 | WT | R248W | N.A. | | sensitive | partial sensitive |
| A549 | WT | WT | G12S | | partial sensitive | partial sensitive |

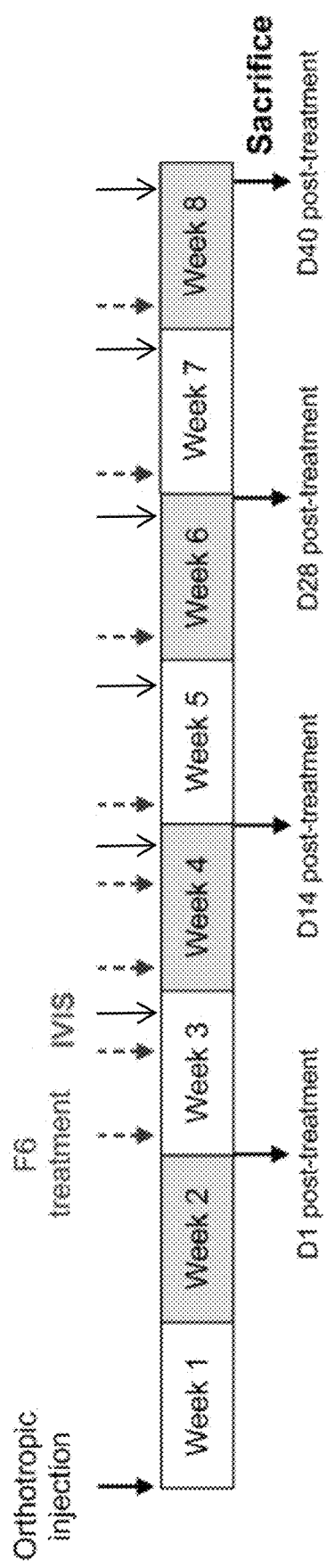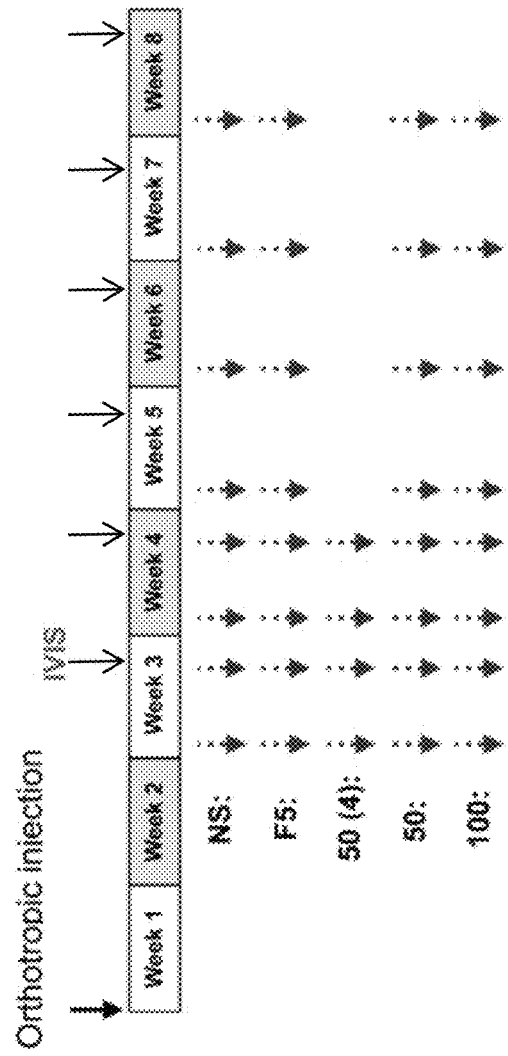

TRIMETHYLGLYCYLGLYCERIN COMPOSITIONS AND THEIR USE IN DEVELOPING ANTI-CANCER DRUGS AND RNA VACCINES

PRIORITY

The present invention claims priority to the U.S. Provisional Application Ser. No. 62/907,666 filed on Sep. 29, 2019, the U.S. Provisional Application Ser. No. 62/936,684 filed on Nov. 18, 2019, and the U.S. Provisional Application Ser. No. 62/949,943 filed on Dec. 18, 2019, all of which were entitled "Novel Trimethylglycylglycerin Compositions for Enhancing Targeted Delivery of Nucleic Acid-Based Drugs via Acetylcholine Receptors In Vivo, Ex Vivo and In Vitro", which are hereby all incorporated by reference as if fully set forth herein.

REFERENCE TO SEQUENCE LISTING SUBMITTED VIA EFS-WEB

This application includes an electronically submitted sequence listing in .txt format. The .txt file contains a sequence listing entitled "5199-0286PWO1 ST25.txt" created on Jul. 7, 2020 and is 1,534 bytes in size. The sequence listing contained in this .txt file is part of the specification and is hereby incorporated by reference herein in its entirety.

FIELD OF INVENTION

This invention generally relates to a group of novel chemical compositions and their use for formulating RNA- and/or DNA-based medicine drugs/vaccines into stable compound complexes useful for in-vitro, ex-vivo and in-vivo delivery. Particularly, the present invention teaches the synthesis of a group of novel trimethylglycyl chemicals and their use for formulating cosmetic, biomedical, therapeutic- and/or pharmaceutical-grade nucleic acid compositions, including but not limited microRNA precursors (pre-miRNA/miRNA), small hairpin RNAs (shRNA), short interfering RNAs (siRNA), ribozymes, antisense synthetic oligonucleotides, RNA-DNA hybrids and DNA-based vectors/vaccines, with or without modification, into delivery complexes, which can then be absorbed by cells in vivo, ex vivo and/or in vitro through an active mechanism of endocytosis via acetylcoline receptors for releasing the cosmetic, biomedical, therapeutic and/or pharmaceutical effects of the formulated nucleic acid compositions. The novelty of the present invention is to create positively charged trimethyl-glycyl-group-containing delivery chemicals for interacting with negatively charged nucleic acid drug compositions via ionic and/or electrostatic affinity, so as to preserve the structural integrity of the nucleic acid compositions for being effectively delivered into target cells via acetylcholine receptors in vivo, ex vivo and/or in vitro. In addition, the present invention further discloses the use of trimethyl-glycyl-modified sugar alcohols and/or sugars to protect small functional and/or therapeutic-grade nucleic acids, in particular pre-miRNA/miRNA, shRNA, siRNA, antisense oligonucleotides, DNA and ribozyme molecules, from degradation and hence preserve their structural integrity and functional effects in vivo, ex vivo as well as in vitro. Therefore, the present invention is not only a group of novel chemical compositions and their use for targeted delivery of nucleic acid-based drugs/vaccines into specific cells via acetylcholine receptors but also a new formula to preserve the structural integrity and functional effects of the nucleic acid-based drugs/vaccines in vivo, ex vivo and/or in vitro.

BACKGROUND

Delivery of functional non-coding RNAs (ncRNA), such as ribozyme, microRNA (miRNA), short hairpin RNA (shRNA) and small interfering RNA (siRNA), is the most difficult obstacle hindering the development of RNA interference (RNAi)-based medicine and therapy for clinical use in vivo. Low penetration and high degradation of these ncRNAs are two of the major problems during in-vivo delivery. In order to overcome these problems, functional ncRNAs must be protected by a delivery agent that is able to not only preserve their structural integrity but also facilitate their uptake by targeted tissue cells in vivo. Yet, none of previously found liposomal or nanoparticle-based delivery agents can fulfill both needs.

Nucleic acid compositions like ribonucleic acids (RNA) and deoxyribonucleic acids (DNA) are negatively charged molecules and hence tend to attract to positively charged materials. On the other hand, the cell membrane consists of phospholipid bilayer, which contains abundant fatty acids and thus is also negatively charged. As a result, naked RNA/DNA will be repelled by the cell membrane and cannot be directly delivered into cells. In order to overcome this problem, one preferred traditional delivery method is liposomal transfection using lipid-based liposomes to encapsulate DNAs/RNAs for intracellular delivery. The mechanism of liposomal transfection is achieved by fusion of liposomes to the phospholipid bilayer of the cell membrane, resulting in passive diffusion of the liposome-encapsulated RNAs/DNAs into the cells. To further improve their delivery efficiency, those liposome molecules are often modified by adding long carbon chains (i.e. glycolipids) or positively charged chemical groups, or both, such as polyethylene glycol [PEG; $H—(O—CH_2—CH_2)_n—OH$] (Immordino et al, 2006), glycerol esters (WO2011143237 to Meyering), glycerol monooleate (Pereira et al, 2002; Zhen et al, 2012), and aminated/amino poly(glycerol methacrylate)s (Gao et al, 2010 and 2011). However, due to their limit by passive diffusion, the efficiency of these liposomal methods is generally not comparable to an active delivery method based on targeted receptor-mediated endocytosis.

In a liposomal delivery system, glycerol is often used as a polymer linker to connect the long carbon chains of fatty acids and phospholipids, such as monooleate and glycerol esters. Modifications in these long carbon chains can form charged chemical groups to interact with DNA/RNA; yet, those charged carbon chains do not possess any ability (i.e. polarity) to protect DNA/RNA from degradation. Alternatively, glycerol also can serve as a side chain in a delivery polymer, such as aminated/amino poly(glycerol methacrylate)s. Those aminated glycerol side chains in such acrylate polymers carry positively charged groups that can form hydrogen bonding (H-bond) with DNA and RNA (Gao et al, 2010). Nevertheless, it is known that the duplex and hairpin structures of DNA and RNA are also formed and maintained by H-bonds. As a result, the H-bonds formed by aminated/amino poly(glycerol methacrylate)s will disturb the structural integrity of DNA/RNA duplexes and hairpins, which are actually required for maintaining the function of many currently known nucleic acid-based drug agents, such as miRNA, shRNA, siRNA, ribozyme, antisense-oligonucleotide and DNA-based medicines and vaccines. Conceivably, none of these liposomal delivery systems can fully protect DNA and RNA from degradation in vivo.

Sugar-based delivery is another preferred transfection method, which is designed to improve the low efficiency and low stability of liposomal delivery methods. Sugar-encapsulated or -conjugated DNAs/RNAs can be absorbed by targeted cells via a receptor-mediated endocytosis mechanism, which increases the concentration and effects of these DNA-/RNA-based medicines in the targeted cells. A variety of carbohydrate compositions have been developed and used in these sugar-based delivery systems, including sugar-based surfactants (EP0535534 to Nair; WO2009029046 to Kim), poly(sugar acrylate) polymers (U.S. Pat. No. 5,618,933 to Dordick), sugar-grafted liposomes (Banerjee et al, 1996), lipid-protein-sugar particles (WO2002032398 to Kohane et al), poly(glycosylated amino acid)s (Davis et al, 2002), lipoamino acid-/glycopeptide- and/or liposaccharide-conjugants (Blanchfield et al, 2004), pectin/chitosan/lecithin nanoparticles (Morris et al, 2010; Cuna et al, 2006; Graf et al, 2008), sugar-PEG-based polymers (Davis et al, 2010; Bhatia et al, 2011), boron-saccharide-based complexes (Ellis et al, 2012), and acetylgalatosamine-conjugants (WO2013074974 to Rajeev; WO2016100716 to Jadhav; U.S. Pat. No. 8,828,956 to Manoharan). However, these sugar-based or sugar-like compositions have not been reported to fully protect the natural structures of RNA and DNA from degradation in vivo. Also, because polysaccharides and sugars do not normally carry any charge, many of these methods still need to be used in conjunction with liposomes or directly covalent conjugation in order to formulate DNAs/RNAs into stable delivery agents. As a result, difficult formulation and chemical modification to the structures of RNA/DNA drugs are another problems.

Recent development of glycylglycerol (glycylglycerin)-based delivery agents are capable of not only protecting the RNA/DNA drugs from degradation but also enhancing the in-vivo delivery of theses RNA/DNA drugs via an active GLUT/SGLT carrier-mediated absorption mechanism into cells (U.S. Pat. No. 9,387,251 to Lin; Lin S L. *Methods Mol Biol.* 1733:305-316, 2018). Nevertheless, a variety of tissue cells express either glucose transporter (GLUT) or sodium-glucose transporter (SGLT) proteins, or both, which therefore can not be served as a target-specific delivery route. In order to overcome this problem and fulfill tissue/organ-targeted delivery via another more specific receptor-mediated absorption mechanism, a further modification of these glycylglycerol agents is needed.

In sum, there is currently no delivery agent that can efficiently deliver RNA-/DNA-based medicines into specific targeted cells while protecting their intact strand structures, particularly duplexes and hairpins, during delivery in vivo. Therefore, it is highly desirable to have a targeted delivery system for efficiently deliver RNA-/DNA-based molecules into specific cells in vivo, ex vivo and/or in vitro while protecting their intact strand structures, in particular duplexes and hairpins.

SUMMARY OF THE INVENTION

Stem cells are like a treasure box containing numerous effective ingredients useful for designing and developing pharmaceutical and therapeutic applications, such as stimulating cell/tissue/organ regeneration, repairing and rejuvenating damaged/aged tissues/organs, treating degenerative diseases (i.e. diabetes, osteoporosis, Parkinson's and Alzheimer's diseases etc.), and preventing tumor/cancer formation, progression and/or metastasis. Hence, we have used stem cells as a tool for novel drug screening, identification, isolation and production as well as studying the mechanism underlying how stem cells produce and preserve these identified drug ingredients. As a breakthrough result, the inventors have disclosed for the first time that certain stem cell-derived chemicals like glycylated sugars and sugar alcohols can protect hairpin-like and duplex RNA molecules, in particular microRNA precursors (i.e. pri- and/or pre-miRNAs), shRNAs, siRNAs and ribozymes, from degradation in human embryonic stem cells (ESCs) and induced pluripotent stem cells (iPSCs) (Chang-Lin et al., *Nucleic Acids Res.* 44:4894-4906, 2016; Lin S L. *Methods Mol Biol.* 1733:305-316, 2018). Due to the structural and physiological similarity of all eukaryotic cells, the identified sugars/sugar alcohols may also provide the same protective effect against the degradation of all hairpin-like and/or duplex RNA species (i.e. microRNAs, shRNAs, siRNAs and ribozymes) in other cell types in vitro as well as in vivo.

Sugar alcohols are a generic kind of polyol alcohols derived from sugars and also frequently called polyhydric alcohol, polyalcohol, or glycitol. As defined in polymer chemistry, polyols are compounds with multiple active hydroxyl groups available for organic reactions and polymeric polyols are usually in a form of polyethers or polyesters. Most sugar alcohols are white, water-soluble natural occurring materials that are often used in the cosmetic, pharmaceutical and food industries as humectants, thickeners and sweeteners. They are represented by a general chemical formula $H(HCHO)_{n+1}H$, which is different from sugars' $H(HCHO)_nHCO$. Also, unlike sugars that tend to form rings, sugar alcohols do not. Yet, they can be dehydrated into cyclic ethers, e.g. sorbitol can be dehydrated to isosorbide. The sugar alcohols differ in chain length and have one hydroxyl (OH) group attached to each carbon (C) molecule in the chain. They are further differentiated by their relative orientation (stereochemistry) of these OH groups; for example, mannitol and sorbitol are isomers that share the same chemical formula $C_6H_8(OH)_6$ but are different in the orientation of the OH group on carbon $2(C^2)$. The common types of sugar alcohols include, but not limited by, alditol, arabitol, erythritol, fucitol, galactitol, glycerol (or called glycerin, glycerine), iditol, inositol, isomalt lactitol, maltitol, mannitol, polyglycitol, ribitol (adonitol), sorbitol, threitol, volemitol, and xylitol. In the present invention, the preferably used sugar alcohols are selected from glycerol (glycerin, glycerine), erythritol, threitol, arabitol, ribitol (adonitol), xylitol, galactitol, iditol, mannitol, and/or sorbitol.

Nucleic acid molecules like deoxyribonucleic acids (DNA) and ribonucleic acids (RNA) are negatively charged materials due to the phosphodiester linkage between consecutive nucleotides and thus they tend to interact with positively charged compounds. However, ions in the water often break down this linkage structure of DNA and particularly RNA strands through a force of hydrolysis and hence cause degradation. To prevent RNA/DNA degradation, alcohol materials are known to carry strong polarity that can expel water molecules out of the strands of RNA and DNA, resulting in stabilizing the structural integrity of RNA and DNA strands. In the present invention, we have tried to use sugar alcohols and/or polysaccharides to encapsulate functional RNAs/DNAs for in-vitro and in-vivo delivery; however, sugar alcohols and sugars usually do not carry any charge or sometimes even carry a slightly negative charge under a low pH condition and hence do not interact well with negatively charged nucleic acids. After studying microRNA miR-302 isolated from human induced pluripotent stem cells (iPSCs), we found that some modified sugars/sugar alcohols are always purified together with miR-302 and are required for stabilizing and protecting the hairpin and duplex structures of miR-302 precursors from degradation. To identify this modified sugar/sugar alcohol, our previous studies had revealed that glycylation is one of the novel sugar/sugar alcohol modifications that promote and enhance the interactions between intracellular sugars/sugar alcohols and RNAs/DNAs, particularly in the hairpin region of microRNA precursors (i.e. pri-/pre-miRNAs) and the duplex region of siRNAs and shRNAs (Chang-Lin et al., *Nucleic Acids Res.* 44:4894-4906, 2016; Lin S L. *Methods Mol Biol.* 1733:305-316, 2018).

Previously, our U.S. Pat. No. 9,387,251 to Lin has demonstrated that glycylation is required for making positively charged sugars/sugar alcohols, which can form stable delivery complexes with either isolated or recombinant RNAs/DNAs and/or RNA/DNA-like synthetic molecules, leading to a very useful application for developing novel medicines and therapies. As defined here, glycylation is a chemical reaction that replaces the hydroxyl (HO—) groups of a sugar alcohol or sugar with glycine's glycyl ($NH_2CH_2COO$—) groups and thus results in the formation of an ether (R—O—R) linkage between each OH-removed carbon of the sugar/sugar alcohol and the glycyl group. For example, as shown in FIG. 1, glycylation of glycerin (glycerol) generates three major kinds of glycylglycerin products: mono-glycyl-glycerin (monoglycylglycerol; MGG; $C5H11O4N1$; MW=149~151 g/mole), di-glycyl-glycerin (diglycylglycerol; DGG; $C7H14O5N2$; MW=206~208 g/mole), and tri-glycyl-glycerin (triglycylglycerol; TGG; $C9H17O6N3$; MW=263~266 g/mole). Under pH<7.4, MGG, DGG and TGG are all positively charged molecules that are able to interact with negatively charged nucleic acids, such as RNA and DNA, and many other kinds of negatively charged drug materials via ionic and/or electrostatic affinity and hence very useful for drug preservation and delivery in vivo, ex vivo as well as in vitro. Moreover, liquid chromatography-mass spectrometry (LC-MS) and stereochemical analyses have further shown that MGG and DGG can also form six- or five-member ring conformations similar to the structures of six-carbon monosaccharides, in particular glucose, fructose and galactose, and thus are capable of being absorbed into cells via GLUT and SGLT carrier proteins. However, because MGG-, DGG-, and TGG-bound RNA/DNA agents are too large to directly pass through these GLUT or SGLT carriers, their absorption into cells likely goes through another active GLUT/SGLT-mediated endocytosis mechanism. Also, since glycylglycerins can form peptide bonds with other amino acids, in particular glycine, the mixture of glycylglycerins and amino acids can further form high-degree polymers, as a layer of sugar-like coating, to facilitate the encapsulation and protection of a variety of nucleic acid-based drugs and vaccines, including pri-/pre-miRNAs, shRNAs, siRNAs and ribozymes.

As GLUT and SGLT carrier proteins exist in almost all cells, glycylglycerins may not be used as a tissue-specific delivery agent for targeted drug delivery. Conceivably, an ordinary skill person in the art may anticipate the modification of glycylglycerins for targeted delivery through other more specific receptor/carrier transportation; yet, direct modification of glycylglycerins is feasible but difficult and the resulting products are very hard to be purified. To overcome this problem, the present invention for the first time discloses a novel chemical reaction, called "trimethyl-glycylation", to generate a group of totally new chemicals, trimethylglycylglycerins (TMGGs) (FIG. 2). Trimethyl-glycylation is a newly discovered chemical reaction that replaces the hydroxyl (HO—) groups of at least a sugar alcohol or sugar with betaine's trimethylglycyl [$(CH_3)_3N^+CH_2COO$—] groups and thus results in the formation of an ether (R—O—R) linkage between each OH-removed carbon of the sugar/sugar alcohol and the trimethylglycyl group. Since betaine is an amino acid "compound", but not a pure amino acid, it is impossible for anyone to foresee the result of this compound reaction in view of the known aminoacylation. In this novel case, a whole new kind of trimethylglycyl (TMG)-containing chemicals is formed by reacting betaine (trimethylglycine) and sugar alcohols, preferably including glycerin (glycerol) and/or ribitol (adonitol)/xylitol, together under a "dehydration condensation" condition at ≥75° C. and 2100 kPa. For example, when glycerin is used, the trimethylglycylation reaction generates at least three major kinds of TMGG products: mono-trimethyl-glycyl-glycerin (mono-TMGG; $C_8H_{18}O_4N_1$ MW=190~193 g/mole; FIG. 3), di-trimethyl-glycyl-glycerin (di-TMGG; $C_{13}H_{28}O_5N_2$ MW=290~293 g/mole; FIG. 4), and tri-trim-ethyl-glycyl-glycerin (tri-TMGG; $C_{18}H_{38}O_6N_3$ MW=390~393 g/mole; FIG. 5). All TMGGs are positively charged and hence can interact with negatively charged nucleic acids, such as RNA and DNA, as well as many other kinds of negatively charged drug materials via ionic bonding and/or electrostatic affinity, leading to a very useful method and application for drug preservation and delivery. Recent LC-MS and stereochemical analyses have further shown that mono- and di-TMGGs can form six- or five-member ring conformations; yet, more preferably interacting with cells via acetylcholine receptors rather than GLUT and SGLT carrier proteins. This unique uptake feature of TMGGs is very different from that of glycylglycerins and thus TMGGs can be used for designing and developing targeted drug delivery agents and methods via acetylcoline receptors.

Betaine is naturally different from acetylcholine and can not function through acetylcholine receptors. However, after modified by trimethylglycylation, the trimethylglycyl (TMG) groups of TMGGs are structurally similar to acetylcholine and hence can interact with a specific group of tissue/organ cells expressing acetylcholine receptors, such as lung and neuron cells. These acetylcholine receptors include nicotinic acetylcholine receptors (nAChR) and muscarinic acetylcholine receptors (mAChR), which are mainly expressed by certain cell types of the central and peripheral nervous systems (CNS and PNS), muscle, heart, the circulation system, and the respiratory system. However, because the size of TMGG-bound nucleic acid agents are too large to pass through blood-brain barrier (BBB), the intravenous injection of TMGG-bound RNA/DNA drugs can not be delivered into the CNS. For treating CNS/neuron-related diseases, such as Alzheimer's disease, Parkinson's disease, Huntington's disease, dementia, meningitis, sclerosis, stroke and brain tumor/cancer, the TMGG-bound RNA/DNA drugs are administered directly into the brain or spine cerebrospinal fluid (CSF) in vivo. Also, due to strong expression of nAChR in lung epithelial and small muscle cells, the spray inhalation of TMGG-containing drugs and/or medicines may be very helpful for treating many respiratory diseases, such as allergy, asthma, bronchitis, coughing, flu, pneumonia, and tumor/cancer.

TMGGs can be further mixed and/or linked with glycylglycerins to generate more effective delivery compounds for tissue-/organ-specific targeted delivery in vivo, ex vivo and/or in vitro. For example, FIG. 6 and FIG. 7 show two important results, but not limited, of the TMGG-glycylglycerin mixture compounds. Accordingly, the high performance liquid chromatography (HPLC) results of trim-ethylglycylation and the mixed trimethylglycylation-glycylation reaction are shown in FIG. 8 and FIG. 9, respectively. FIG. 6 shows that when glycylation occurs before trimethylglycylation, the mixed reaction can generate 2-trimethylglycyl-1,3-di-glycylglycerin (2-TMG-1,3-DGG) and few 1- or 3-TMG-DGGs. These mono-TMG-DGGs possess a chemical formula C12H25O6N3 and each molecular weight MW=305~308 g/mole. Among them, the 2-TMG-1,3-DGG compound is important because its 1,3-DGG part can bind to the minor grooves of the hairpin and duplex structures of pri-/pre-miRNA, shRNA, siRNA and ribozyme for preventing degradation, while its 2-TMG part is responsible for specifically interacting with acetylcholine receptors for targeted drug delivery. Also, all mono-TMG-DGGs can be further reacted and connected with other amino acids, particularly glycine, to form polymers, which can further facilitate drug delivery and protection (FIG. 10). On the other hand, FIG. 7 shows that when glycylation and trimethylglycylation occur almost at the same time under a relatively lower temperature, the mixed reaction mainly generates mono-TMG-MGGs, such as 1-TMG-3-MGG, 3-TMG-1-MGG, 2-TMG-1-MGG, 2-TMG-3-MGG, 1-TMG-2-MGG, and/or 3-TMG-2MGG. All of these mono-TMG-MGGs possess a chemical formula C10H22O5N2 and each weights about MW=248~251 g/mole. Mono-TMG-MGGs can also be further integrated into other liposomes, nanoparticles, and/or conjugants for modifying these delivery chemicals into acetylcholine receptor-specific delivery agents. Also, since the amino groups of mono-TMG-MGGs can form peptide bonds with other weak acids and amino acids, in particular glycine, the mixture of mono-TMG-MGGs and amino acids can further form high-degree polymers, served as a layer of acetylcholine-like ligand coating, to facilitate the drug uptake via acetylcholine receptors (FIG. 10). Conceivably, there are many more possible pharmaceutical/therapeutic compositions and methods that can be designed and developed using the isoforms and derivatives of these novel various TMGG, TMG-DGG, TMG-MGG and TMGG-glycylglycerin molecules, of which their potential utilizations are highly desirable and expected. The designs and methods mentioned above are particularly useful for developing targeted delivery agents for cosmetic, biomedical, pharmaceutical and therapeutic applications.

Since trimethylglycylated sugar alcohols/sugars can interact with all sorts of negatively charged materials (including organic or inorganic chemical compounds) for targeted delivery via acetylcholine receptors in vivo, ex vivo and in vitro, they are herein useful for developing a variety of therapeutic, pharmaceutical, biomedical and cosmetic products, devices as well as applications for clinical, non-clinical and/or research use. For example, in one preferred embodiment, as shown in FIG. 11, trimethylglycylated and/or glycylated sugar alcohols/sugars can be used to encapsulate and formulate functional microRNAs (i.e. pri-/pre-miRNA/shRNA) and/or their siRNA/shRNA mimics into therapeutic drugs/vaccines for eliciting specific RNA interference (RNAi) effects against a variety of diseases, including, but not limited to, allergy, asthma, bronchitis, dementia, diabetes, flu, meningitis osteoporosis, pneumonia, sclerosis, stroke, motor neuron disease (MND), Parkinson's, disease Alzheimer's disease, Huntington's disease (HD), and tumors/cancers. To this point, it has been noted that many microRNAs (pre-miRNAs/miRNAs) and their siRNA mimics, in particular miR-34, miR-142, miR-146 and miR-302, are well-known tumor suppressors which can be used for silencing oncogenes and treating various human tumors/cancers, including but not limited, liver, lung, skin, bone, prostate, breast cancers and brain tumors as well as leukemia [Lin et al., (2008) RNA 14:417-424; (2008) *RNA* 14:2115-2124; (2010) *Cancer Research* 70:9473-9482].

Moreover, these trimethylglycylated and TMG-glycylglycerin-mixed sugars/sugar alcohols may be applied to protect and deliver vector-based DNA/RNA drugs and/or vaccines that are frequently used for non-viral gene therapy and/or anti-viral treatments. In another preferred embodiment, as shown in FIG. 12, these TMGG-, glycylglycerin- and/or TMGG-glycylglycerin-formulated nucleic acid-based drugs and/or vaccines can be effectively delivered into target cells to elicit specially designed RNAi effects and the following immune responses directed against viral infection, cancer progression/metastasis, and/or various genetic disease formation. For example, we had designed and developed at least three different types of siRNAs/shRNAs targeting against coronavirus's RNA-dependent RNA polymerase (RDRP) and capsid gene sequences, respectively, in the viral RNA genome. These targeted gene regions in the viral genome are relatively conserved and evolutionally preserved. The sequences of these three siRNA/shRNA constructs are synthetic RNA sequences containing either 5'-GUUGGUUGCC AUAACAAGUG UGC-3' (SEQ.ID.NO.1), 5'-GAUAAAGGAG UUGCACCAGG UAC-3' (SEQ.ID.NO.2), or 5'-CUACCGAAGA GCUACCAGAC GAA-3' (SEQ.ID.NO.3), and their matched antisense sequences. After delivered into targeted cells (particularly into the lung cells via acetylcholine and/or glucose/fructose receptors in this case), the designed siRNAs and/or shRNAs will degrade a part of the viral genome and make the viral genes into fragments. After that, since there is no intact viral genome and no RDRP or caspid, mature virus can not be produced! Also, some of the degraded viral gene fragments may still continue to make viral proteins (such as spike, membrane, and/or surface proteins), which can be excluded out of the infected cells and then induce immune responses to generate antibodies directed against the viral infection. In this way, patients can be not only cured but also immunized to fight against the viral infection. Clearly, by the same token, this our design and utilization of RNAi-mediated immunization can be applied to fight against other kinds of RNA and DNA viruses, including, but not limited to, human immunodeficiency virus (HIV), hepatitis B virus (HBV), hepatitis C virus (HCV), human papillomavirus (HPV), influenza viruses and many other pathogenic RNA viruses. Since short RNA synthesis is fast, easy and relatively cheap, in combination with our currently invented TMGG-, glycylglycerin- and/or TMGG-glycylglycerin-based delivery agents, a new kind of powerful and inexpensive RNA vaccines can be abundantly and quickly produced to fight against various infectious diseases. Expectedly, a novel way of vaccine production is highly desired in view of our design (FIG. 12).

In view of the aforementioned embodiments, it is conceivable that the present invention can be used for developing various biomedical products, drugs and/or vaccines for the use in various cosmetic, pharmaceutical and therapeutic designs, devices and applications.

A. Definitions

To facilitate understanding of the invention, a number of terms are defined below:

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. A nucleoside containing at least one phosphate group bonded to the 3' or 5' position of the pentose is a nucleotide. DNA and RNA are consisted of different types of nucleotide units called deoxyribonucleotide and ribonucleotide, respectively.

Olitonucleotide: a molecule comprised of two or more DNAs and/or RNAs, preferably more than three, and usually more than ten. An oligonucleotide longer than 13 nucleotide monomers is also called polynucleotiude. The exact size will depend on many factors, which in turn depends on the ultimate function or use of the oligonucleotide. The oligonucleotide may be generated in any manner, including chemical synthesis, DNA replication, RNA transcription, reverse transcription, or a combination thereof.

Nucleotide Analog: a purine or pyrimidine nucleotide that differs structurally from adenine (A), thymine (T), guanine (G), cytosine (C), or uracil (U), but is sufficiently similar to substitute for the normal nucleotide in a nucleic acid molecule.

Nucleic Acid Composition: a nucleic acid composition refers to a natural or synthetic oligonucleotide or polynucleotide, such as a DNA or RNA sequence, or a mixed DNA/RNA hybrid sequence, in either a single-stranded or a double-stranded molecular structure.

Gene: a nucleic acid composition whose oligonucleotide or polynucleotide sequence codes for an RNA and/or a polypeptide (protein). A gene can be either RNA or DNA. A gene may encode a non-coding RNA, such as small hairpin RNA (shRNA), microRNA (miRNA), rRNA, tRNA, snoRNA, snRNA, and their RNA precursors as well as derivatives.

Alternatively, a gene may encode a protein-coding RNA essential for protein/peptide synthesis, such as messenger RNA (mRNA) and its RNA precursors as well as derivatives. In some cases, a gene may encode a protein-coding RNA that also contains at least a microRNA or shRNA sequence.

Primary RNA Transcript: an RNA sequence that is directly transcribed from a genetic DNA without any RNA processing or modification, which may be selected from the group consisting of hnRNA, pre-mRNA, rRNA, tRNA, snoRNA, snRNA, pri-microRNA (pri-miRNA), viral RNA and their RNA precursors as well as derivatives. After transcription, uracil (U) is substituted for thymine (T).

Precursor messenger RNA (pre-mRNA): primary messenger RNA transcripts of a protein-coding gene, which are produced by eukaryotic type-II RNA polymerase (Pol-II) machineries in eukaryotes through an intracellular mechanism termed transcription. A pre-mRNA sequence contains a 5'-untranslated region (UTR), a 3'-UTR, exons and introns.

Messenger RNA (mRNA): assembly of pre-mRNA exons, which is formed after intron removal by intracellular RNA splicing machineries (spliceosomes) and served as a protein-coding RNA for peptide/protein synthesis. The peptides/proteins encoded by mRNAs include, but not limited, enzymes, growth factors, insulin, antibodies and their analogs/homologs as well as derivatives.

Complementary DNA (cDNA): a single-stranded or double-stranded DNA that contains a sequence complementary to an mRNA sequence and does not contain any intronic sequence.

Sense: a nucleic acid molecule in the same sequence order and composition as the homologous mRNA. The sense conformation is indicated with a "+", "s" or "sense" symbol.

Antisense: a nucleic acid molecule complementary to the respective mRNA molecule. The antisense conformation is indicated as a "−" or "*" symbol or with an "a" or "antisense" in front of the DNA or RNA, e.g., "aDNA" or "aRNA".

Base Pair (bp): a partnership of adenine (A) with thymine (T), or of cytosine (C) with guanine (G) in a double stranded DNA molecule. In RNA, uracil (U) is substituted for thymine. Generally the partnership is achieved through hydrogen bonding. For example, a sense nucleotide sequence "5'-A-T-C-G-U-3'" can form complete base pairing with its antisense sequence "5'-A-C-G-A-T-3'".

5'-end: a terminus lacking a nucleotide at the 5' position of successive nucleotides in which the 5'-hydroxyl group of one nucleotide is joined to the 3'-hydroyl group of the next nucleotide by a phosphodiester linkage. Other groups, such as one or more phosphates, may be present on the terminus.

3'-end: a terminus lacking a nucleotide at the 3' position of successive nucleotides in which the 5'-hydroxyl group of one nucleotide is joined to the 3'-hydroyl group of the next nucleotide by a phosphodiester linkage. Other groups, most often a hydroxyl group, may be present on the terminus.

Template: a nucleic acid molecule being copied by a nucleic acid polymerase. A template can be single-stranded, double-stranded or partially double-stranded, depending on the polymerase. The synthesized copy is complementary to the template, or to at least one strand of a double-stranded or partially double-stranded template. Both RNA and DNA are synthesized in the 5' to 3' direction. The two strands of a nucleic acid duplex are always aligned so that the 5' ends of the two strands are at opposite ends of the duplex (and, by necessity, so then are the 3' ends).

Nucleic Acid Template: a double-stranded DNA molecule, double stranded RNA molecule, hybrid molecules such as DNA-RNA or RNA-DNA hybrid, or single-stranded DNA or RNA molecule.

Conserved: a nucleotide sequence is conserved with respect to a pre-selected (referenced) sequence if it non-randomly hybridizes to an exact complement of the pre-selected sequence.

Homologous or Homology: a term indicating the similarity between a polynucleotide and a gene or mRNA sequence. A nucleic acid sequence may be partially or completely homologous to a particular gene or mRNA sequence, for example. Homology may be expressed as a percentage determined by the number of similar nucleotides over the total number of nucleotides.

Complementary or Complementarity or Complementation: a term used in reference to matched base pairing between two polynucleotides (i.e. sequences of an mRNA and a cDNA) related by the aforementioned "base pair (bp)" rules. For example, the sequence "5'-A-G-T-3'" is complementary to the sequence "5'-A-C-T-3'", and also to "5'-A-C-U-3'". Complementation can be between two DNA strands, a DNA and an RNA strand, or between two RNA strands. Complementarity may be "partial (imperfect)" or "complete (perfect)" or "total". Partial complementarity or complementation occurs when only some of the nucleic acid bases are matched according to the base pairing rules. Complete or total complementarity or complementation occurs when the bases are completely or perfectly matched between the nucleic acid strands. The degree of complementarity between nucleic acid strands has significant effects on the efficiency and strength of hybridization between nucleic acid strands. This is of particular importance in amplification reactions, as well as in detection methods that depend on binding between nucleic acids. Percent complementarity or complementation refers to the number of mismatch bases over the total bases in one strand of the nucleic acid. Thus, a 50% complementation means that half of the bases were mismatched and half were matched. Two strands of nucleic acid can be complementary even though the two strands differ in the number of bases. In this situation, the complementation occurs between the portion of the longer strand corresponding to the bases on that strand that pair with the bases on the shorter strand.

Complementary Bases: nucleotides that normally pair up when DNA or RNA adopts a double stranded configuration.

Complementary Nucleotide Sequence: a sequence of nucleotides in a single-stranded molecule of DNA or RNA that is sufficiently complementary to that on another single strand to specifically hybridize between the two strands with consequent hydrogen bonding.

Hybridize and Hybridization: the formation of duplexes between nucleotide sequences which are sufficiently complementary to form complexes via base pairing. Where a primer (or splice template) "hybridizes" with target (template), such complexes (or hybrids) are sufficiently stable to serve the priming function required by a DNA polymerase to initiate DNA synthesis. There is a specific, i.e. non-random, interaction between two complementary polynucleotides that can be competitively inhibited.

RNA Interference (RNAi): a posttranscriptional gene silencing mechanism in eukaryotes, which can be triggered by small inhibitory RNA molecules such as microRNA (miRNA), small hairpin RNA (shRNA) and small interfering RNA (siRNA). These small RNA molecules usually function as gene silencers, interfering with either expression of intracellular genes or translation of the gene transcripts, or both, that contain certain target sequences either completely or partially complementarity to the small RNAs.

Gene Silencing Effect: a cell response after a gene function is suppressed, consisting of, but not limited, inhibition of oncogene expression, inhibition of cell proliferation, cell cycle arrest, tumor suppression, cancer regression, cancer prevention, cell apoptosis, cell repairing and/or rejuvenation, cell reprogramming, reprogramming diseased cells to a relatively normal state (spontaneous healing), and a combination thereof.

Non-coding RNA: an RNA transcript that cannot be used to synthesize peptides or proteins through intracellular translation machineries. Non-coding RNA includes long and short regulatory RNA molecules such as microRNA (miRNA), small hairpin RNA (shRNA), small interfering RNA (siRNA) and double strand RNA (dsRNA). These regulatory RNA molecules usually function as gene silencers, interfering with expression of intracellular genes containing either completely or partially complementarity to the non-coding RNAs.

MicroRNA (miRNA): single-stranded RNA capable of binding to targeted gene transcripts (mRNAs) that have partial complementarity to the sequence of microRNA. Mature microRNA is usually sized about 17-27 oligonucleotides in length and is able to either directly degrade its intracellular mRNA target(s) or suppress the protein translation of its targeted mRNA(s), depending on the complementarity between the microRNA and its target mRNA(s). Native microRNAs are found in almost all eukaryotes, functioning as a defense against viral infections and allowing regulation of specific gene expression during development of plants and animals. In principle, one microRNA often target multiple target mRNAs to fulfill its full functionality while on the other hand multiple miRNAs may target the same gene transcripts to enhance the effect of gene silencing.

MicroRNA Precursor (pri-/pre-miRNA): hairpin-like single-stranded RNA containing stem-arm and stem-loop regions for interacting with RNase III Dicer endoribonucleases to produce one or multiple mature microRNAs (miRNAs) capable of silencing a targeted gene or a specific group of targeted genes that contain full or partial complementarity to the mature microRNA sequence(s). The stem-arm of a pri-/pre-miRNA can form either a perfectly (100%) or a partially (mis-matched) hybrid duplexes, while the stem-loop connects one end of the stem-arm duplex to form a circle or hairpin-loop conformation required for being assembled into an RNA-induced silencing complex (RISC) with some argonaute proteins (AGO).

Small interfering RNA (siRNA): short double-stranded RNA sized about 18-27 perfectly base-paired ribonucleotide duplexes and capable of degrading target gene transcripts with almost perfect complementarity.

Small or short hairpin RNA (shRNA): single-stranded RNA that contains a pair of partially or completely matched stem-arm nucleotide sequences divided by an unmatched loop oligonucleotide to form a hairpin-like structure. Many natural miRNAs are derived from hairpin-like RNA precursors, namely precursor microRNA (pre-miRNA).

Vector: a recombinant nucleic acid composition such as recombinant DNA (rDNA) capable of movement and residence in different genetic environments. Generally, another nucleic acid is operatively linked therein. The vector can be capable of autonomous replication in a cell in which case the vector and the attached segment is replicated. One type of preferred vector is an episome, i.e., a nucleic acid molecule capable of extrachromosomal replication. Preferred vectors are those capable of autonomous replication and expression of nucleic acids. Vectors capable of directing the expression of genes encoding for one or more polypeptides and/or non-coding RNAs are referred to herein as "expression vectors" or "expression-competent vectors". Particularly important vectors allow cloning of cDNA from mRNAs produced using a reverse transcriptase. A vector may contain components consisting of a viral or a type-II RNA polymerase (Pol-II or pol-2) promoter, or both, a Kozak consensus translation initiation site, polyadenylation signals, a plurality of restriction/cloning sites, a pUC origin of replication, a SV40 early promoter for expressing at least an antibiotic resistance gene in replication-competent prokaryotic cells, an optional SV40 origin for replication in mammalian cells, and/or a tetracycline responsive element. The structure of a vector can be a linear or circular form of single- or double-stranded DNA selected form the group consisting of plasmid, viral vector, transposon, retrotransposon, DNA transgene, jumping gene, and a combination thereof.

Promoter: a nucleic acid to which a polymerase molecule recognizes, or perhaps binds to, and initiates RNA transcription. For the purposes of the instant invention, a promoter can be a known polymerase or its cofactor binding site, an enhancer and the like, any sequence that can initiate synthesis of RNA transcripts by a desired polymerase.

Targeted Cell: a single or a plurality of human cells selected from the group consisting of a somatic cell, a tissue cell, a stem cell, a germ-line cell, a teratoma cell, a tumor cell, a cancer cell, and a combination thereof.

Cancerous Tissue: a neoplastic tissue derived from the group consisting of skin cancer, prostate cancer, breast cancer, liver cancer, lung cancer, brain tumor/cancer, lymphoma, leukemia and a combination thereof.

Gene Delivery: a genetic engineering method selected from the group consisting of polysomal transfection, liposomal transfection, chemical transfection, electroporation, viral infection, DNA recombination, transposon insertion, jumping gene insertion, microinjection, gene-gun penetration, and a combination thereof.

Genetic Engineering: a DNA recombination method selected from the group consisting of DNA restriction and ligation, homologous recombination, transgene incorporation, transposon insertion, jumping gene integration, retroviral infection, and a combination thereof.

Tumor Suppression Effect: a cellular anti-tumor and/or anti-cancer mechanism and response consisting of, but not limited, cell cycle attenuation, cell cycle arrest, inhibition of tumor cell growth, inhibition of cell tumorigenecity, inhibition of tumor/cancer cell transformation, induction of tumor/cancer cell apoptosis, induction of normal cell recovery, reprogramming high-grade malignant cancer cells to a more benign low-grade state (tumor regression), and a combination thereof.

Cancer Therapy Effect: a cell response and/or cellular mechanism resulted from a drug treatment, including, but not limited, inhibition of oncogene expression, inhibition of cancer cell proliferation, inhibition of cancer cell invasion and/or migration, inhibition of cancer metastasis, induction of cancer cell death, prevention of tumor/cancer formation, prevention of cancer relapse, suppression of cancer progression, repairing damaged tissue cells, reprogramming high-grade malignant cancers to a more benign low-grade state (cancer regression/remission), and a combination thereof.

Cancer Reversion: a reprogramming mechanism that resets the malignant properties of high-grade cancers back to a relatively normal-like low-grade state in vitro, ex vivo or in vivo.

Glycylation: a chemical reaction that replaces the hydroxyl (HO—) groups of a sugar alcohol or sugar with glycine's glycyl ($NH_2CH_2COO$—) groups and thus results in the formation of an ether (R—O—R) linkage between each OH-removed carbon of the sugar alcohol/sugar and the glycyl group of the glycine.

Trimethylglycylation: a chemical reaction that replaces the hydroxyl (HO—) groups of a sugar alcohol or sugar with betaine's trimethylglycyl [$(CH_3)_3N^+CH_2COO$—] groups and thus results in the formation of an ether (R—O—R) linkage between each OH-removed carbon of the sugar/sugar alcohol and the trimethylglycyl group.

Pharmaceutical and Therapeutic Application: a biomedical utilization, treatment method, device and/or apparatus useful for diagnosis, stem cell generation, stem cell research and/or therapy development, tissue/organ repair and/or rejuvenation, wound healing treatment, tumor suppression, cancer therapy and/or prevention, disease treatment, drug production, and a combination thereof.

B. Compositions and Applications

A composition and its use for formulating nucleic acid compositions with sugar alcohols into delivery complexes for both in-vitro, ex vivo and in-vivo delivery into mammalian cells via acetylcholine receptors, comprising: (a) at least a nucleic acid composition with at least a negative charge, and (b) at least a sugar alcohol or sugar modified by trimethylglycylation; wherein (a) and (b) are mixed together under a condition to form delivery complexes. The nucleic acid composition can be microRNA precursors (miRNA), small hairpin RNAs (shRNA), short interfering RNAs (siRNA), ribozymes, antisense RNAs/DNAs, RNA-DNA hybrids, DNA vectors/vaccines, and a combination thereof. The condition required for the delivery complex formation is under a dehydration condensation condition at $\geq 75°$ C. and $\geq 100$ kPa.

In principle, the present invention teaches a novel method of trimethylglycylation and its use for generating positively charged sugar alcohol and/or sugar compounds capable of interacting with negatively charged nucleic acid compositions via ionic bonding and/or electrostatic affinity rather than covalent conjugation. Since such ionic/electrostatic affinity is formed between the trimethylglycyl groups of the modified sugars/sugar alcohols and the phosphodiester-linked backbones of RNAs/DNAs, the attached sugars/sugar alcohols can then repel water molecules away from the RNA/DNA backbones, so as to prevent hydrolysis and thus protect the intact structures of these nucleic acid compositions for better delivery of their drug effects into cells in vivo as well as in vitro.

In addition, the present invention discovered that chemical compounds containing TMGGs and/or TMGG-glycylglycerin mixture structures not only can protect the integrity of nucleic acid-based drug compositions, such as miRNA, shRNA, siRNA, ribozyme and DNA, from degradation but also provide a targeted delivery mechanism via acetylcholine receptors. Hence, the present invention is not only a composition and its use for delivering nucleic acid-based drugs/vaccines into cells but also a material formula for preserving the structural integrity and functional efficacy of these nucleic acid-based drugs and/or vaccines in vivo as well as in vitro. Due to these novel features, the present invention is very useful for developing and/or improving a variety of nucleic acid-based cosmetic, pharmaceutical and therapeutic applications.

BRIEF DESCRIPTION OF THE DRAWINGS

Referring particularly to the drawings for the purpose of illustration only and not limitation, there is illustrated:

FIG. 3 shows the chemical reaction of trimethylglycylation and the resulting mono-trimethylglycylglycerins (mono-TMGGs) thereof.

FIG. 4 shows the chemical reaction of trimethylglycylation and the resulting di-trimethylglycylglycerins (di-TMGGs) thereof.

FIG. 6 shows the mixed reaction of trimethylglycylation and glycylation together, which mainly generates mono-trimethylglycyl-di-glycylglycerins (mono-TMG-DGGs; $C12H25O6N3$; molecular weight around MW=305~308 g/mole) and their derivatives thereof.

FIG. 7 shows the mixed reaction of glycylation first and then trimethylglycylation, of which the reaction mainly generates mono-trimethylglycyl-mono-glycylglycerins (mono-TMG-MGGs; $C10H22O5N2$; MW=248~251 g/mole) thereof.

FIG. 10 shows the formation of TMGG-glycylglycerin polymers. The mixture reaction of mono-TMG-MGGs, mono-TMG-DGGs, and/or TMGG with other amino acids, particularly glycine, can form a variety of high-degree structural polymers through peptide bonding and/or electrostatic/ionic affinity.

As shown in FIG. 11, the induced RNAi effects then directly degrade and/or prevent the translation of the target RNAs, which contain complementary strand sequences to the mature miRNAs and/or siRNAs. The target RNAs include, but not limited to, viral genomes (viron; particularly RNA virus virons), oncogenes (particularly mutated cancer genes), and pathogenic genes that cause human diseases. It is further noticed that, since the RNAi effects only degrade or block a part of the target RNAs, the remaining target RNA fragments may still be translated into some small pieces of proteins, such as viral and/or cancer marker proteins, which are then excluded out of the cells for inducing immune responses and generating antibodies against the viruses and/or diseases (i.e. cancers).

FIG. 14A demonstrated the bar-chart results of the inhibitory effect of F6 on the colony number and size of human malignant lung cancer A 549 cell line. FIG. 14B showed the photos of the average cancer colony sizes before and after different F6 treatments, from left to right: control (original cancers treated with PBS), F5 (treated with the glycylglycerin-based formulation solution only), F6-25 (treated with 25 µg/mL F6), and F6-50 (treated with 50 µg/mL F6), respectively.

FIG. 15 shows the mutation status of several driver genes in a variety of different human lung cancer cell lines and types, including the mutant types of EGFR, p53, and K-ras oncogenes (as shown on the panels to the left of the middle column of pictures of the different cancer cell colonies). The middle column of FIG. 15 shows the pictures of cancer colonies formed by original cancer cells derived from four different human lung cancer cell lines (types) without any treatment, whereas the panels to the right of the middle column of pictures display the inhibitory effect of one F6 treatment (50 µg/mL) on the colony formation of these different lung cancer types, of which the resulting drug potency is categorized into four groups: sensitive (reduced >50% in the average colony size), partial sensitive (reduced 25~50%), partial resistant (reduced <25%), and resistant groups (no effect 0%).

FIG. 17A demonstrated the numbers of lung cancer nodules found in different treatment and control groups of mice, and FIG. 17B showed the representative photo pictures of all lung cancer tissues found in both of the treatment and control groups, respectively. FIG. 17C showed the histological examination results of typical lung adenocarcinoma structures (circled and pointed by a black arrow).

FIGS. 18A and 18B show the time schedule flowchart of treatment frequency (18A) and image taking frequency (18B) of the second animal trial experiments using a formulated pre-miR-302 (F6) drug to treat highly malignant and metastatic human NSCLC implants in mice.

FIG. 19A demonstrated the numbers of lung cancer nodules found in different treatment and control groups of mice, and FIG. 19B showed the representative photo pictures of all lung cancer tissues found in both of the treatment and control groups, respectively. FIG. 19C showed lymphocyte infiltration, a typical anti-cancer immune response in effect, in the implanted tumors/cancers after the F6 treatments (circled and pointed by a black arrow), of which the immune response may be likely induced by the RNAi-mediated mechanism as shown in FIG. 12.

EXAMPLES

In the experimental disclosure which follows, the following abbreviations apply: M (molar); mM (millimolar); μm (micromolar); mol (moles); pmol (picomoles); gm (grams); mg (milligrams); μg (micrograms); ng (nanograms); L (liters); ml (milliliters); μl (microliters); ° C. (degrees Centigrade); RNA (ribonucleic acid); DNA (deoxyribonucleic acid); dNTP (deoxyribonucleotide triphosphate); PBS (phosphate buffered saline); NaCl (sodium chloride); HEPES (N-2-hydroxyethylpiperazine-N-2-ethanesulfonic acid); HBS (HEPES buffered saline); SDS (sodium dodecyl sulfate); Tris-HCl (tris-hydroxymethylaminomethane-hydrochloride); ATCC (American Type Culture Collection, Rockville, Md.); hESC (human embryonic stem cells); and iPSC (induced pluripotent stem cells).

1. MicroRNA (miRNA) Production and Isolation and siRNA Synthesis

Dicer-negative cells were acquired from Zymo Research (Irvine, Calif.), transduced with a pre-made miR-302 expression lentiviral vector pLenti-EF lalpha-RGFP-miR302 (Mello Biotech, Santa Fe Springs, Calif.), and maintained according to manufacturers' suggestions. MicroRNAs and microRNA precursors were isolated with a mirVana™ miRNA isolation kit (Ambion, Austin, Tex.), following the manufacturer's protocol. The isolated miRNAs (for example, pre-miR-302) were dissolved in autoclaved 1× Tris buffer at a concentration up to 5 mg/mL and stored at −80° C. till use. For stability tests with HPLC, a desired amount of the isolated RNAs was re-collected with an Amicon Ultra-0.5 mL 30K filter column (Millipore, Billerica, Mass.) and re-dissolved in autoclaved normal saline. For siR-302 preparation, synthetic miR-302 mimics were purchased from Sigma-Genosys (St. Louis, Mo.), containing two cyanine 5.5 (Cy5.5)-labeled RNA sequences: 5'-Cy5.5-UAAGUGCUUC CAUGUUUUAG UGU-3' (SEQ.ID.NO.4) and 5'-Cy5.5-ACACUAAAAC AUG-GAAGCAC UUA-3' (SEQ.ID.NO.5). In experiments, siR-302 was formed by the hybrids of SEQ.ID.NO.4 and SEQ.ID.NO.5.

2. Trimethylglycylation of Sugar Alcohols and Formulation of miRNA/shRNA/siRNA

Figure 1:
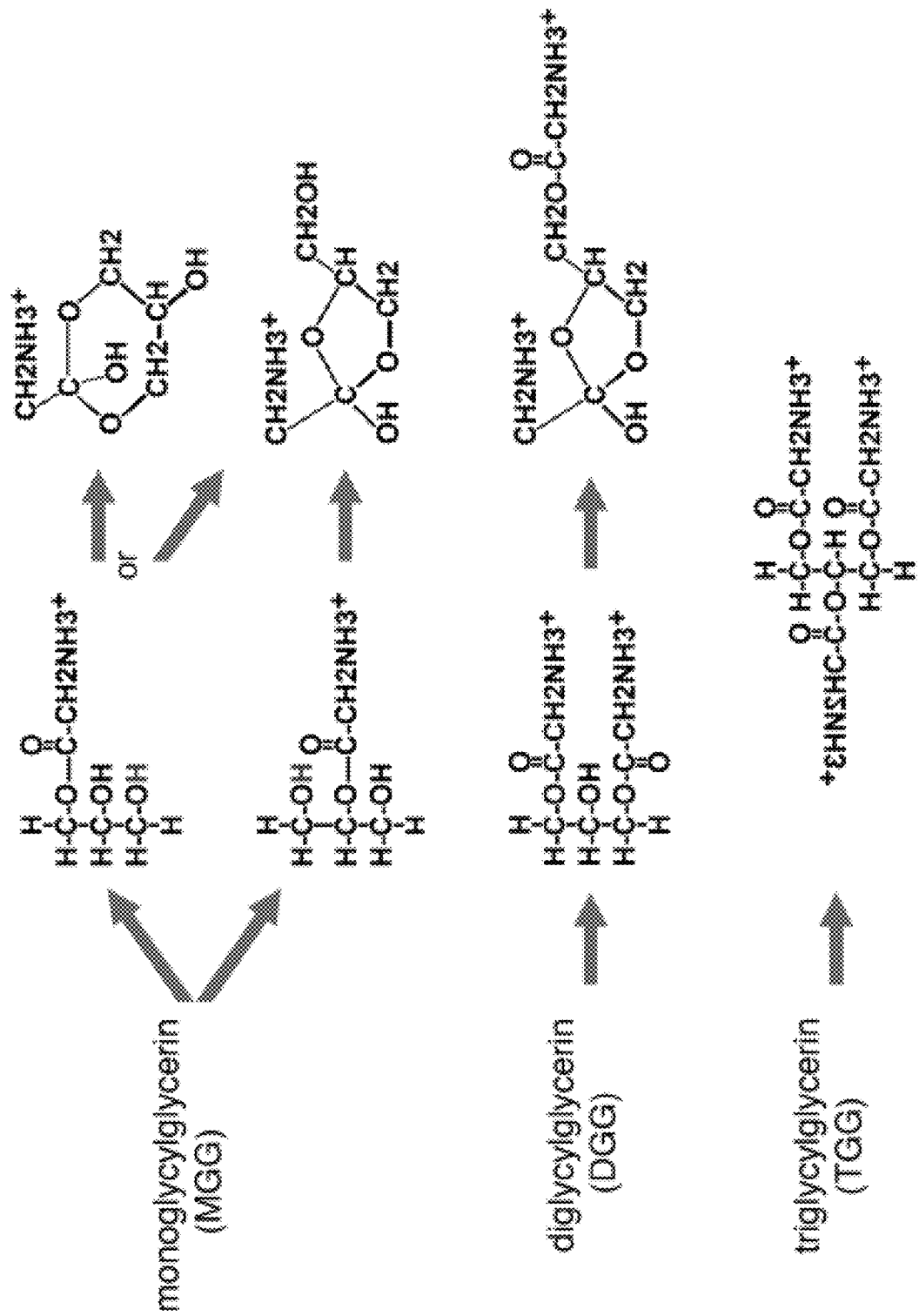
FIG. 1 shows the three major groups of glycylation-derived products, including mono-glycylglycerins (MGG; $C_5H_{11}O_4N_1$; each molecular weight around MW=149~151 g/mole), di-glycylglycerins (DGG; $C_7H_{14}O_5N_2$; MW=206~208 g/mole), and tri-glycylglycerin (TGG; $C_9H_{17}O_6N_3$; MW=263~266 g/mole). MGG and DGG are partially glycylated products, while TGG is a completely (or fully) glycylated product. MGG and DGG can further form six- or five-member ring conformations similar to the chemical structures of six-carbon monosaccharides, in particular glucose, fructose and galactose, and thus are capable of being absorbed into cells via GLUT and SGLT carrier proteins.
Figure 2:
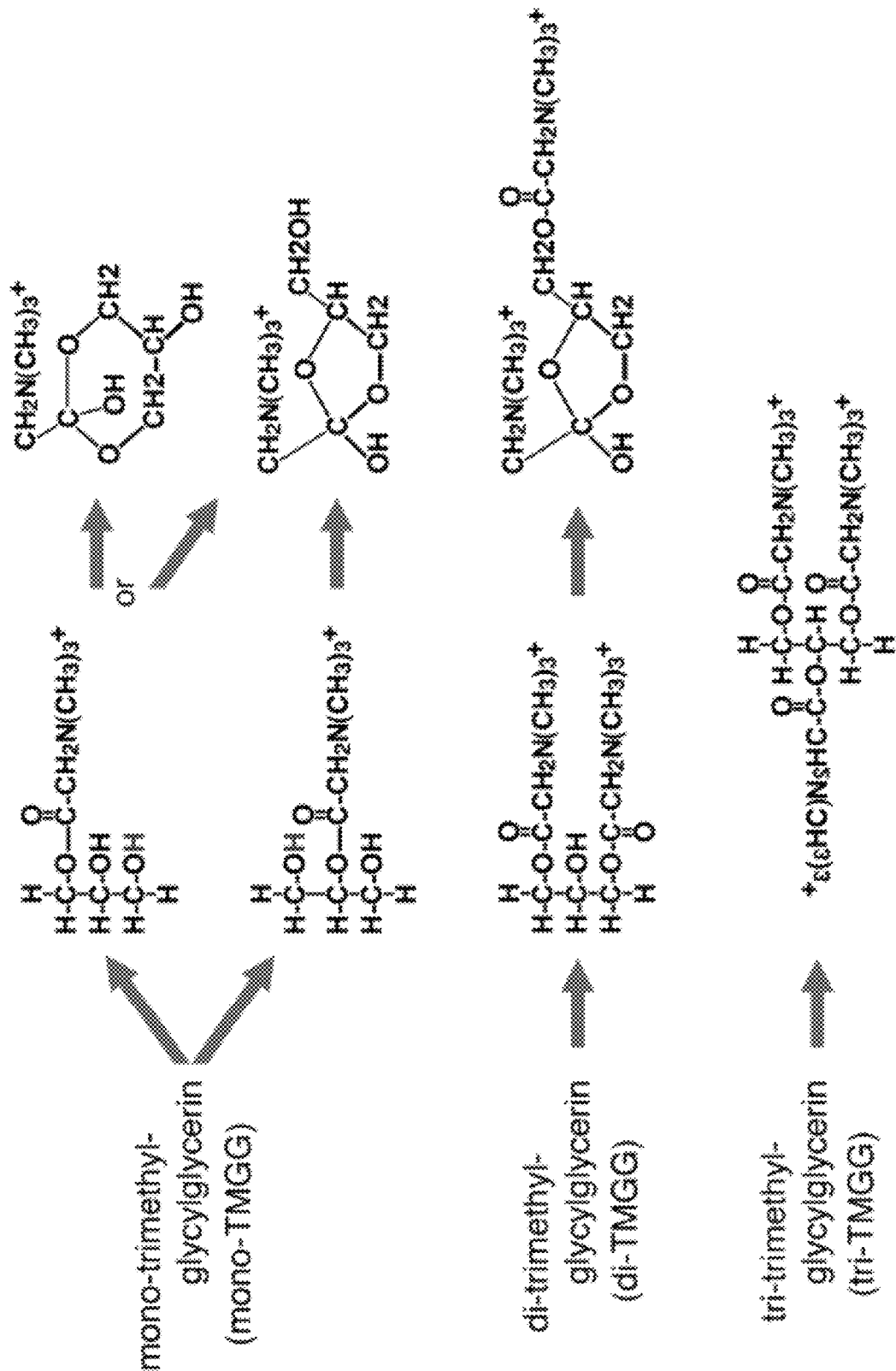
FIG. 2 shows the three major groups of trimethylglycylation-derived products, including mono-trimethylglycylglycerins (mono-TMGG; $C_8H_{18}O_4N_1$; each molecular weight around MW=190~193 g/mole), di-trimethylglycylglycerins (di-TMGG; $C_{13}H_{28}O_5N_2$; molecular weight around MW=290~293 g/mole) and tri-trimethylglycylglycerin (tri-TMGG; $C_{18}H_{38}O_6N_3$; MW=390~393 g/mole). Mono- and di-TMGGs can further form six- and/or five-member ring conformations similar to the chemical structures of six-carbon monosaccharides; yet, all TMGGs preferably interact with acetylcholine receptors rather than GLUT/SGLT carrier proteins because the containing trimethylglycyl group highly resembles acetylcholine. This unique feature of TMGGs is completely different from glycylglycerins.
Figure 5:
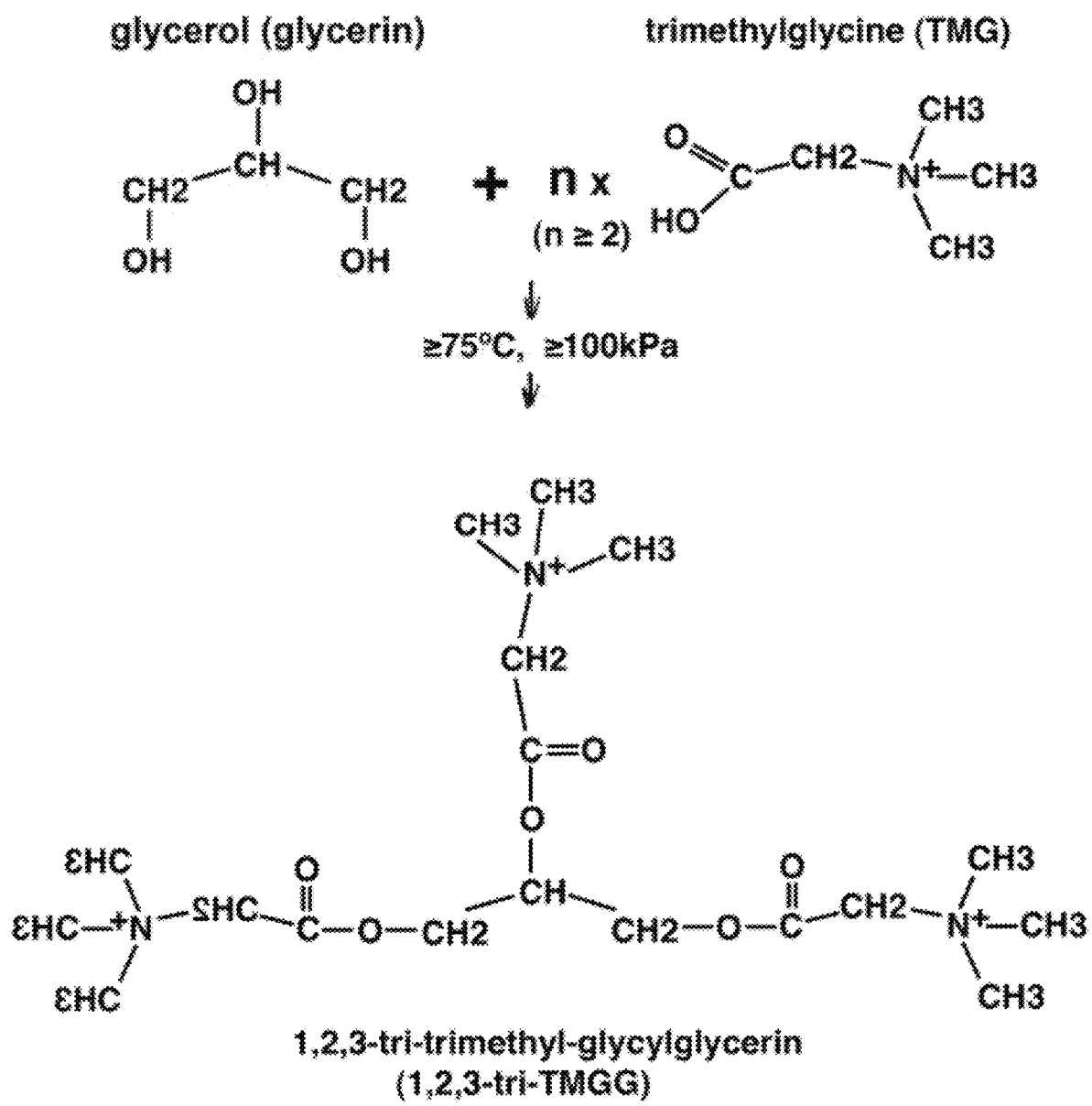
FIG. 5 shows the chemical reaction of trimethylglycylation and the resulting tri-trimethylglycylglycerin (tri-TMGG) thereof.
Figure 8:
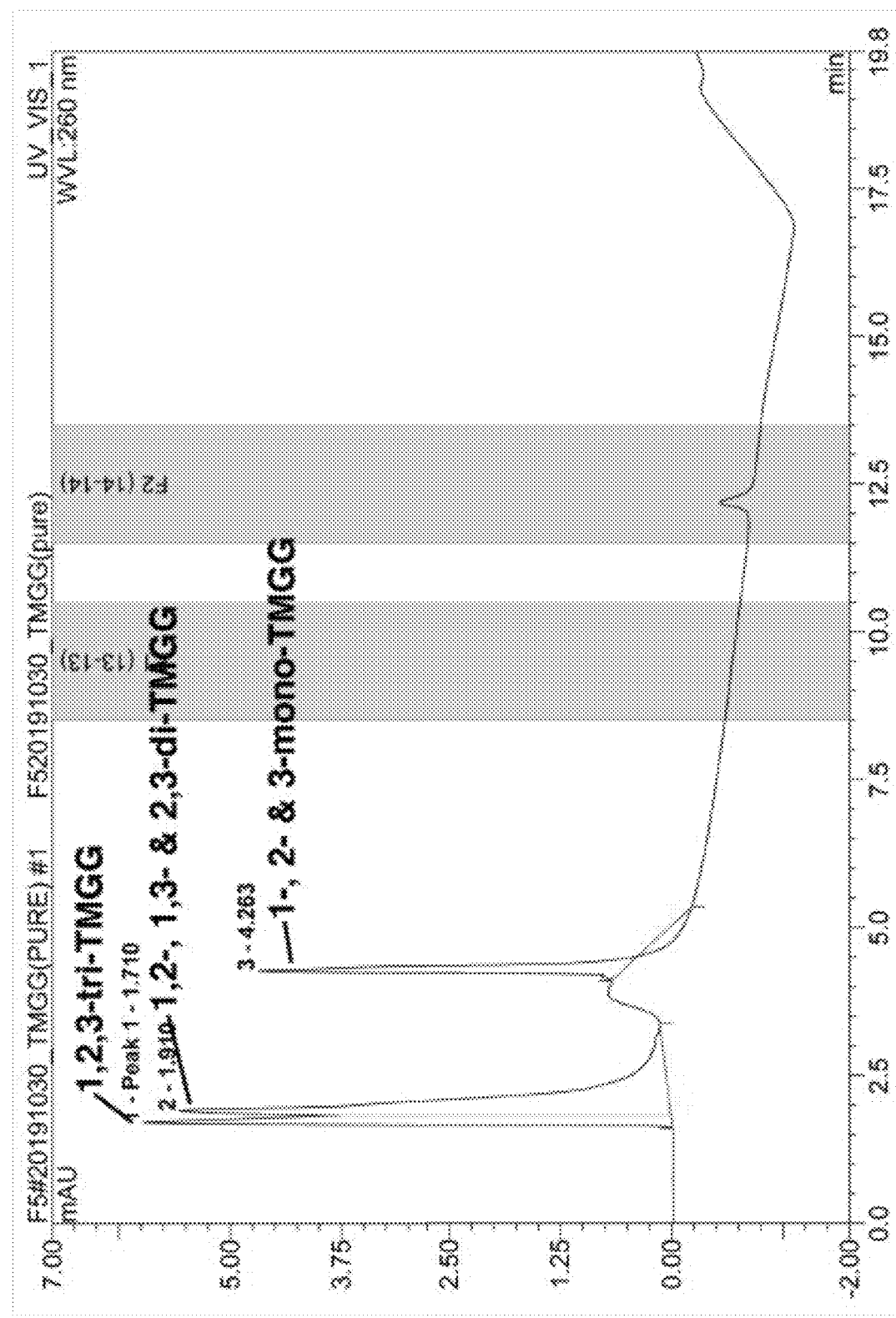
FIG. 8 shows high performance liquid chromatography (HPLC) analyses of the results of trimethylglycylation between betaine (trimethylglycine, TMG) and glycerin (or called glycerol).
Figure 9:
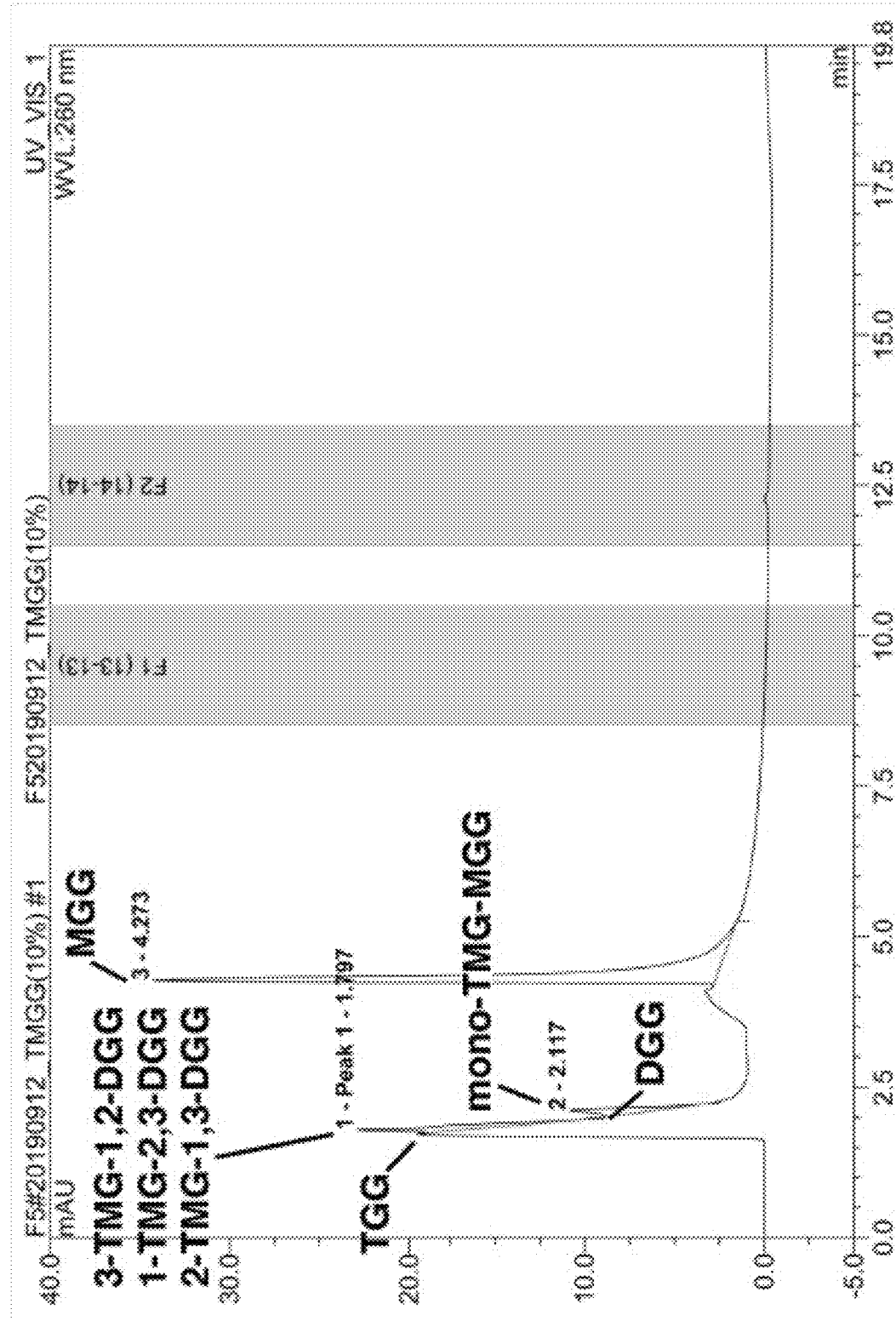
FIG. 9 shows high performance liquid chromatography (HPLC) analyses of the results of trimethylglycylation among betaine (trimethylglycine, TMG), glycine and glycerin (or called glycerol).
Figure 11:
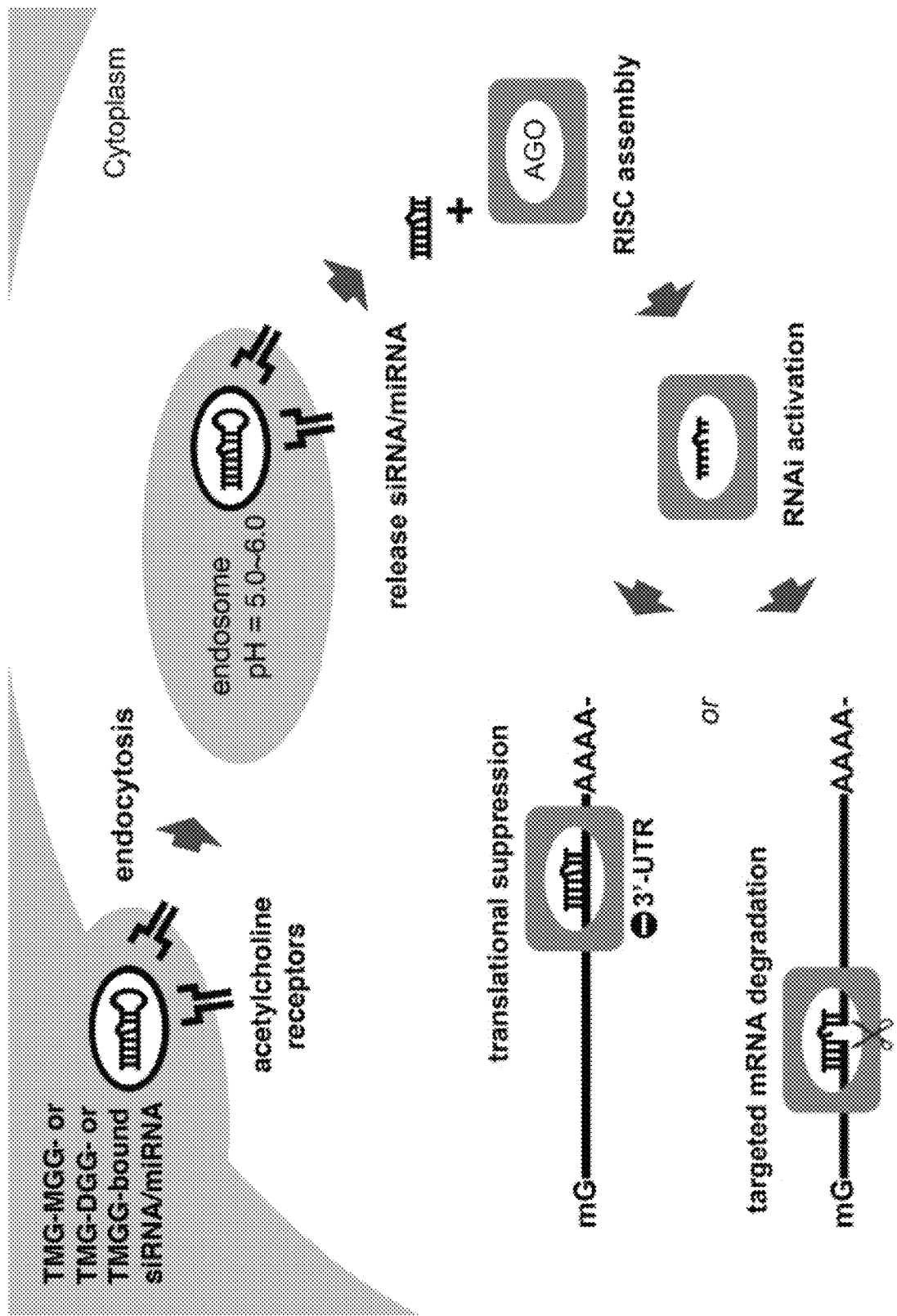
FIG. 11 shows the TMGG- and/or TMG-glycylglycerin-mediated nucleic acid-based drug delivery pathway and the following induced RNA interference (RNAi) effects thereof.
Figure 12:
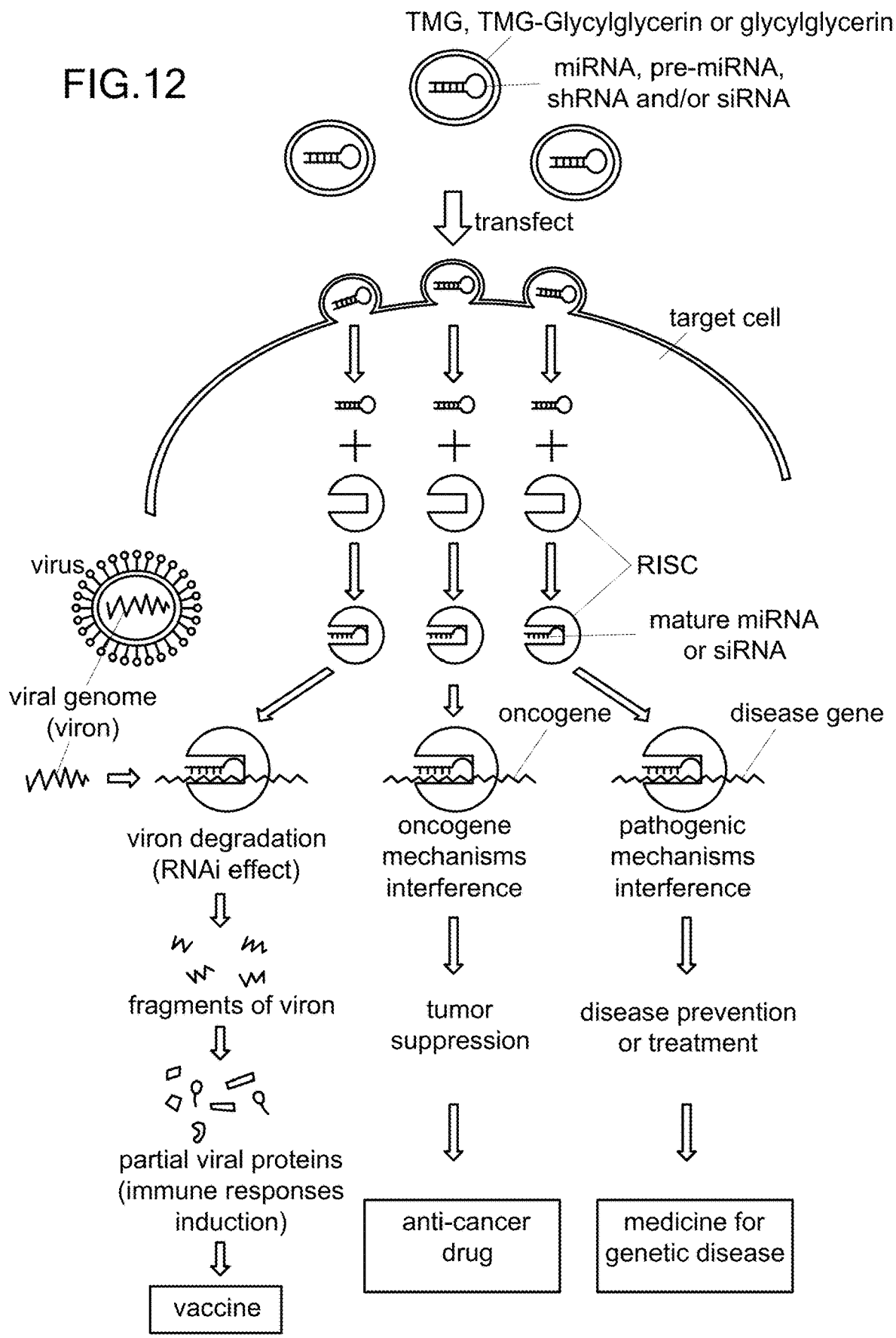
FIG. 12 shows the formulation of anti-cancer drugs and/or RNA vaccines, using TMGG-, glycylglycerin- and/or TMGG-glycylglycerin-based delivery agents, and the related delivery and induced RNAi mechanisms thereof. In brief, these TMGG-, glycylglycerin- and/or TMGG-glycylglycerin-formulated nucleic acid-based drugs and/or vaccines are first delivered into target cells via either acetylcholine- or glucose/fructose-receptor-mediated endocytosis, depending on which delivery agents. After endocytosis, endosomes digest the delivery agents and release the anti-cancer drug and/or RNA vaccines, for example, such as pre-miRNAs/miRNAs and siRNAs. Intracellular Dicer RNases then further modify and protect the designed anti-cancer drugs and/or RNA vaccines to form mature miRNAs and/or siRNAs. Then, intracellular Argonaute (AGO) proteins, Dicer RNases and other RNAi-related proteins together form RNA-induced silencing complexes (RISC) around the mature miRNAs and/or siRNAs in order to elicit RNAi effects.

Although the natural way of sugar/sugar alcohol glycylation is unclear, we have developed a chemical procedure to artificially make glycylated sugar alcohols and sugars. First, a pre-made base solution was prepared, containing 0~5.0M, preferably 0.1~2.0M glycerin (glycerol) and/or other substitutive sugar alcohols, such as xylitol and erythritol, and/or 0~1.0M fructose/glucose (optional), and/or about 0.45%~0.90% NaCl (w/v; optional) at around pH2.5~pH8.0, depending on the source and amount of sugar alcohol(s) used. For activating trimethylglycylation, about 0.01~10.0M, preferably 0.5~5.0M, of USP-grade betaine (TMG) and 0~2.0M glycine were added and mixed into the pre-made base solution, depending on the desired concentration and type(s) of final trimethylglycylated (TMG) and/or trimethylglycylated-(TMG)-glycylated-mixed sugar alcohol products. The final trimethylglycylated (TMG) sugar alcohol products may include mono-trimethyl-glycyl-glycerin (mono-TMGG; $C_8H_{18}O_4N_1$; FIG. 3), di-trimethyl-glycyl-glycerin (di-TMGG; $C_{13}H_{28}O_5N_2$; FIG. 4), and/or tri-trimethyl-glycyl-glycerin (tri-TMGG; $C_{18}H_{38}O_6N_3$; FIG. 5) as well as optional mono-trimethyl-glycyl-erythritol/xylitol, di-trimethyl-glycyl-erythritol/xylitol and/or tri-trimethyl-glycyl-erythritol/xylitol. Alternatively, the final products may also contain TMG-glycylated-mixed sugar alcohols, including but not limited to 2-trimethylglycyl-1,3-di-glycylglycerin (2-TMG-1,3-DGG), 1-TMG-2,3-DGG and/or 3-TMG-1,2-DGG as well as 2- or 3-mono-trimethylglycyl-1,4-di-glycylerythritol, 2-, 3- or 4-mono-trimethylglycyl-1,5-di-glycylxylitol, 2-/3-, 2-/4- or 3-/4-di-trimethylglycyl-1,5-di-glycyl-xylitol and some other mono- and/or di-trimethyl-glycyl-MGG/glycylerythritol/glycylxylitol compositions These different resulting products can be further separately purified and collected using HPLC. Then, this mixed solution was incubated under a dehydration condensation condition at ≥75° C. and ≥100 kPa, most preferably about between 100° C. and 160° C. at about between 101 kPa and 250 kPa (about 14~37 psi or about 1~25 bar). When the final volume of the mixed solution was reduced to about or over a half of the starting solution volume due to dehydration, the trimethylglycylation reaction was completed and the final products were ready to be further separately purified and used for formulating and delivering negatively charged materials, such as nucleic acid and similar chemical compositions. The principle of this novel formulation is based on the electrostatic affinity and/or ionic bonding between the trimethyl glycylated and/or the TMG-glycylated-mixed sugar alcohols and the nucleic acid compositions to form encapsulated delivery complexes, which can then be absorbed by cells through an active acetylcholine receptor-mediated endocytosis mechanism. For demonstration, a schematic trimethylglycylation reaction using glycerin as an example was shown in FIGS. 3, 4 and 5.

3. Human Cell Culture and Transfection

Human lung epithelial cell line and lung cancer cell lines were purchased from ATCC and cultivated according to manufacturer's protocols at 37° C. under 5% $CO_2$. Cells were passaged at about 50%-70% confluence by exposing the cells to trypsin/EDTA for about 1 min and then rinsing two times in HBSS containing trypsin inhibitor. The detached cells were replated at 1:5 dilutions in fresh EpiLife medium with HKGS supplements. For miRNA transfection, pri-/pre-miR-302 prepared from Example 1 was dissolved in 0.01~5.0M, preferably 0.1~2.0M, of TMGG solution at a desired concentration up to 5 mg/ml and then directly applied to cell culture medium based on the miRNA amount needed. For example, to deliver 200 pri-/pre-miR-302, we would need to add 40 μl of the TMGG-dissolved pri-/pre-miR-302 (at 5 mg/ml) into the cell culture medium and then mix well with the cells. Since TMGG is extremely safe and non-toxic, the tested cells could be cultivated in 0.01~3.0M TMGG, preferably 0.1~1.0M TMGG, with all necessary supplements and still not showing any adverse effect up to 48 hours.

4. High Performance Liquid Chromatography (HPLC) Analysis

A reverse-phase HPLC method was developed for analyzing the purity and structural integrity of miR-302 and its precursors (i.e. pre-miR-302s). HPLC programs were run by an Ultimate 3000 HPLC machine (Thermo Scientific) with a DNA Pac PA-100 column (BioLC Semi-Prep 9×250 mm)

at a flow rate of 3.6 ml/min. Starting buffer was 50 mM Tris-HCl (pH7.6) and mobile buffer was 50 mM Tris-HCl (pH7.6) with 500 mM sodium perchlorate. Signals of RNAs and DNAs were measured with an UV detector at 260 nm.

5. MicroRNA (miRNA) Microarray Analysis

At about 70% confluency, small RNAs from each cell culture were isolated, respectively, using the mirVana™ miRNA isolation kit (Ambion). The purity and quantity of the isolated RNAs were assessed, using 1% formaldehyde-agarose gel electrophoresis and spectrophotometer measurement (Bio-Rad), and then immediately frozen in dry ice and submitted to LC Sciences (San Diego, Calif.) for miRNA microarray analyses. Each microarray chip was hybridized with a single sample labeled with either Cy3 or Cy5 or a pair of samples labeled with Cy3 and Cy5, respectively. Background subtraction and normalization were performed as manufacturer's suggestions. For a dual sample assay, a p-value calculation was performed and a list of differentially expressed transcripts more than 3-fold (yellow-red signals) was produced.

6. Formulation Using TMGG and/or TMG-Glycylglycerin Delivery Agents

For enhancing the in-vitro and in-vivo delivery of DNA/RNA-based drugs and/or vaccines, the nucleic acid drug or vaccine compositions were first dissolved in a proper amount of autoclaved ddH2O, normal saline, Tris buffer or TE buffer at their highest possible soluble concentrations and then directly mixed with the pre-prepared TMGG and/or TMG-glycylglycerin delivery agents to reach a proper concentration for the use in treatments. Different treatments may require different concentrations of the TMGG and/or TMG-glycylglycerin-formulated nucleic acid drugs or vaccines for the best therapeutic results. For example, for testing toxicity, we injected 200 µg of synthetic siR-302 (from Example 1) dissolved in 200 µl of 0.1~2.0M, preferably 0.5~1.0M, TMGG or TMG-MGG/TMG-DGG solution into each of C57BL/6J strain mice via tail vein injection. Approximately 24 hours post-injection, we sacrificed two mice for observing the TMGG- and/or TMG-MGG-/TMG-DGG-delivered siR-302 distribution in vivo. As these siR-302 molecules were labeled with infra-red fluorescent dye Cy5.5, we could directly observe their in-vivo distribution using a bio-imaging system and/or their fluorescent signals in mouse tissue sections under a fluorescent microscope.

7. In Vitro Lung Cancer Sensitivity to Drug Tests

Figure 13:
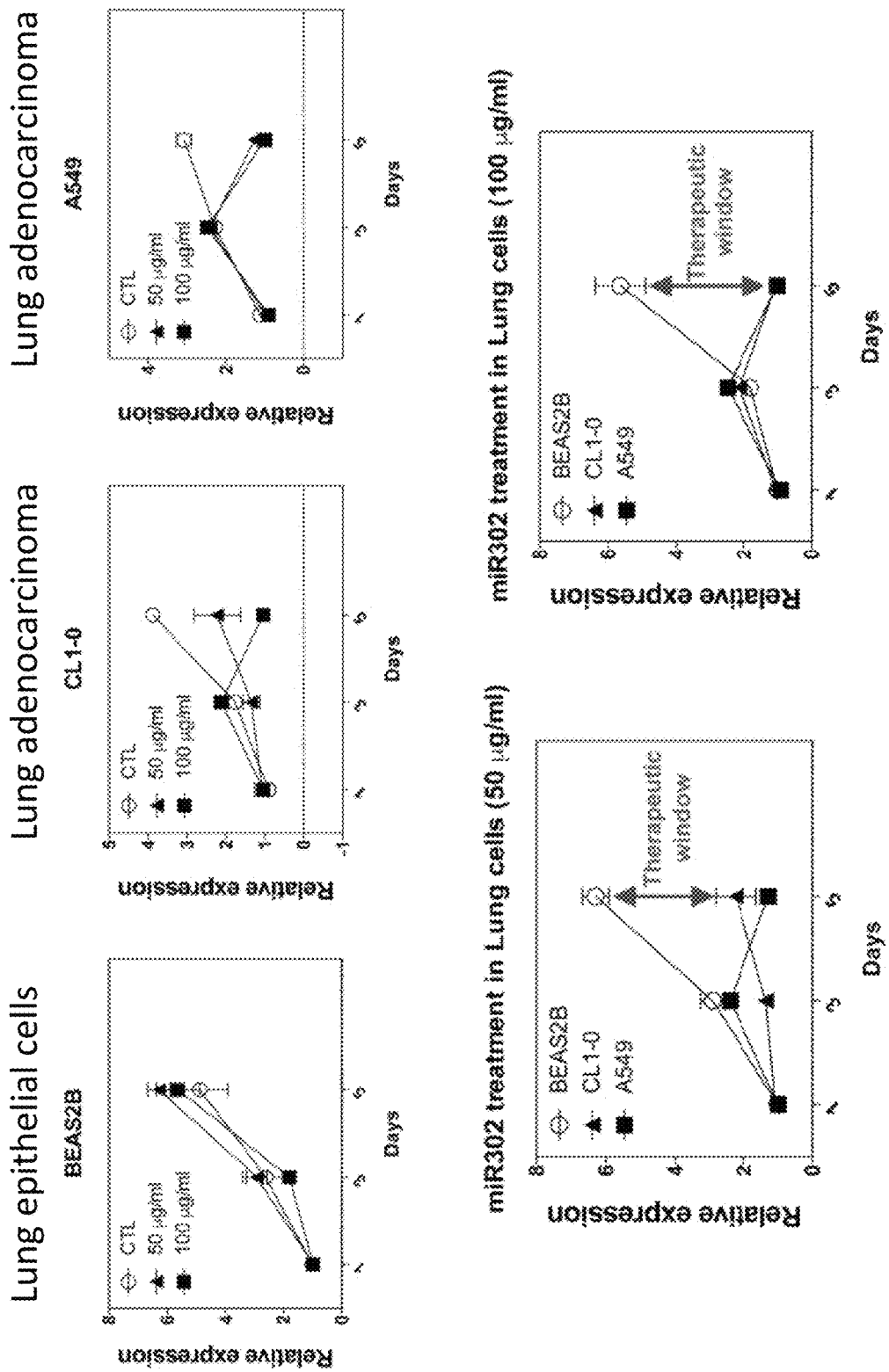
FIG. 13 shows the results of dose-dependent cancer therapy using formulated pre-miR-302 as an anti-cancer drug for treating normal lung epithelial cell line BEAS2B (top left), cancerous lung adenocarcinoma tissue cells isolated from a lung cancer patient CL1-0 (top middle), and lung adenocarcinoma tissue cells isolated from another cancer patient A549 (top right) as well as the dose-dependent therapeutic results of these lung cancers in response to pre-miR-302 treatments at two different concentrations of 50 (bottom left) and 100 (bottom right) microgram (µg)/mL, respectively.
Figure 14A:
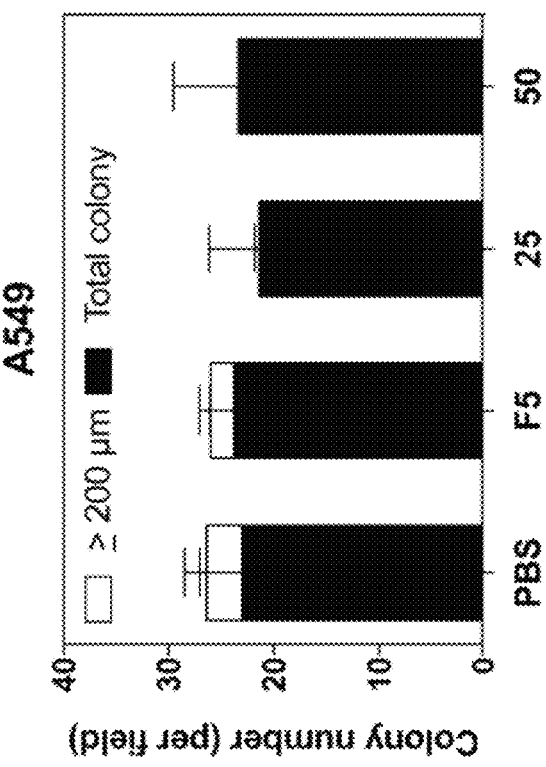
FIGS. 14A and 14B show the therapeutic potency of a formulated pre-miR-302 (F6) drug directed against the growth of malignant lung cancer cells in vitro, using a soft agar colony formation assay.
Figure 14B:
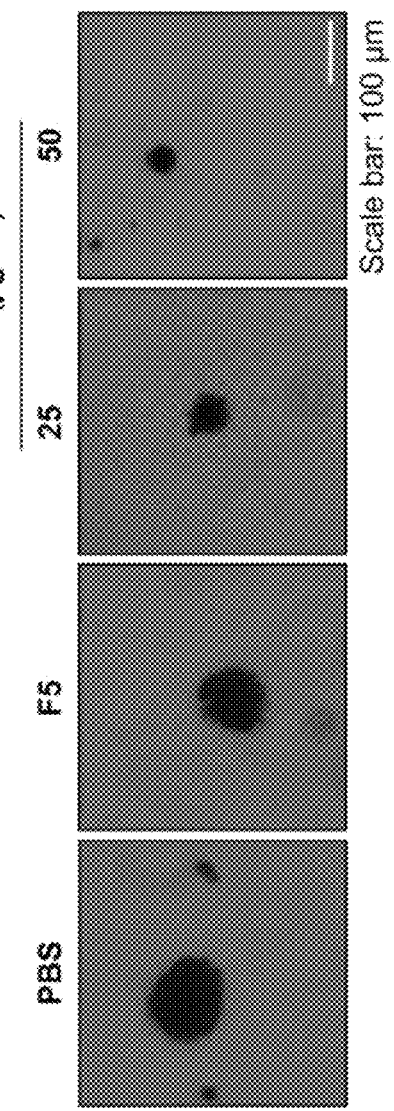

TMGG-, glycylglycerin- and TMG-glycylglycerin-formulated nucleic acid drugs can elicit the same RNAi effects to silence pathogenic genes (such as oncogenes and viral genes), but through different carrier-protein-mediated endocytosis mechanisms. For lung cancer therapy, since lung cancer cells carry abundant GLUT and acetylcholine (particularly nicotinic) receptors, all three delivery agents will provide almost the same delivery results and RNAi effects on the treated cancer cells. For example, as shown in FIG. 13, the dose-dependent tumor suppression effect of a glycylglycerin-encapsulated pre-miR-302/shRNA drug (or called formula #6; F6) on the growth proliferation of different lung cancer cell types was tested, using various pre-miR-302 concentrations ranged from 0 to 200 µg/mL, preferably between 25~100 µg/mL. In order to further test the F6 drug potency against the growth of malignant lung cancer cells, a soft agar colony formation assay was performed, as shown in FIGS. 14A and 14B. The results showed that both of the growth and colony formation abilities of a typical human malignant lung cancer cell line A549 were markedly inhibited after one F6 treatment (either 25 or 50 µg/mL), especially in the population of large size colonies (diameter ≥200 µm). In addition, FIG. 15 further demonstrated the mutation status of several driver oncogenes in a variety of different human lung cancer cell types, including the status of mutated EGFR, p53, and K-ras oncogenes. The middle column of FIG. 15 shows the pictures of cancer colonies formed by original cancer cells of four different human malignant/metastatic lung cancer cell lines (types) without any treatment, whereas the panels to the right of the middle column display the inhibitory effect of one F6 treatment (50 µg/mL) on the colony formation of these lung cancer types, of which the resulting drug potency in these cancer cell types was categorized into four groups: sensitive (reduced >50% in the average colony size), partial sensitive (reduced 25~50%), partial resistant (reduced <25%), and resistant groups (0%).

8. In Vivo Lung Cancer Therapy Trials

Figure 16A:
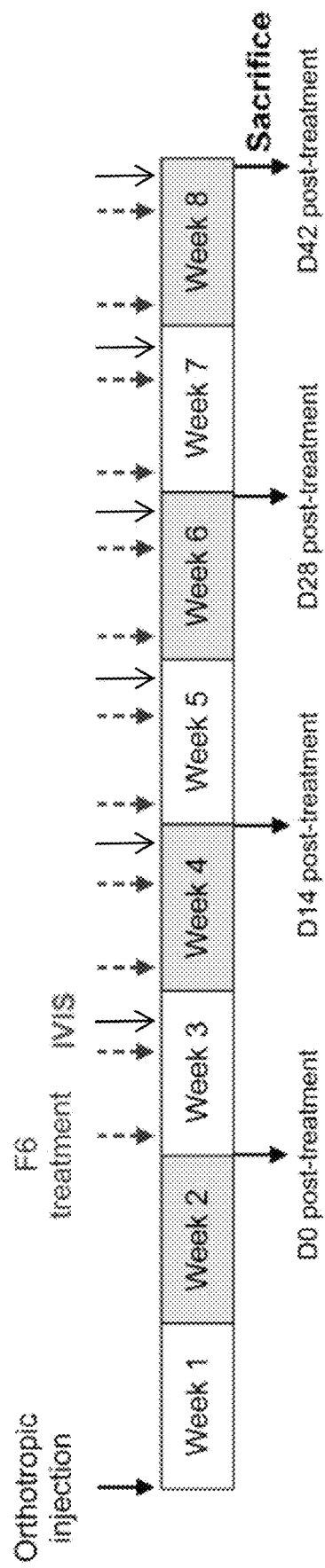
FIGS. 16A and 16B show the time schedule flowchart of treatment frequency (16A) and image taking frequency (16B) of the first animal trial experiments using a formulated pre-miR-302 drug, called F6, to treat highly malignant and metastatic human lung cancer implants in mice.
Figure 16B:
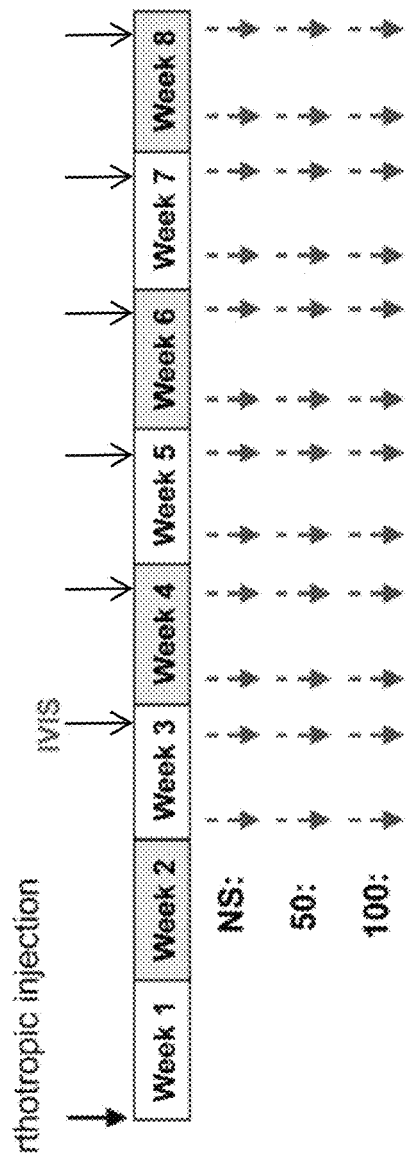
Figure 17B:
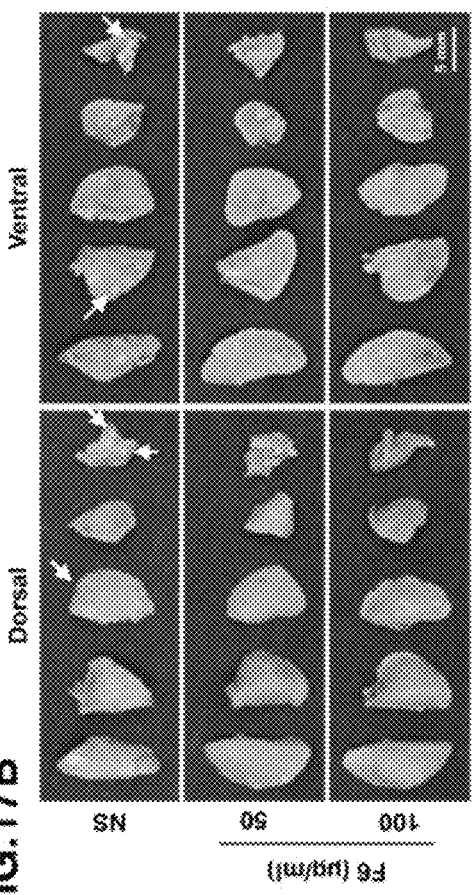
FIGS. 17A, 17B and 17C show the therapeutic results of the first animal trial experiments using a formulated pre-miR-302 drug, called F6, to treat highly malignant and metastatic human lung cancer implants in mice.
Figure 17A:
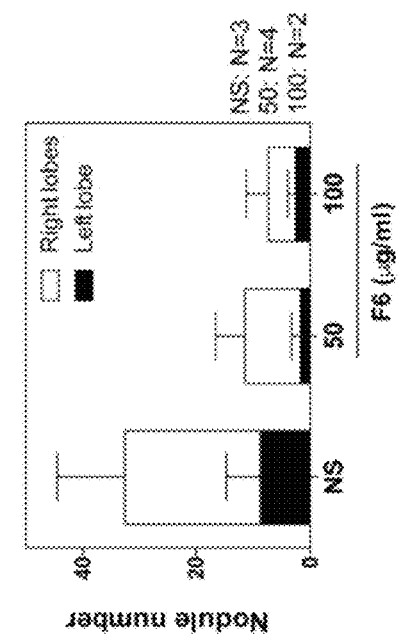
Figure 17C:
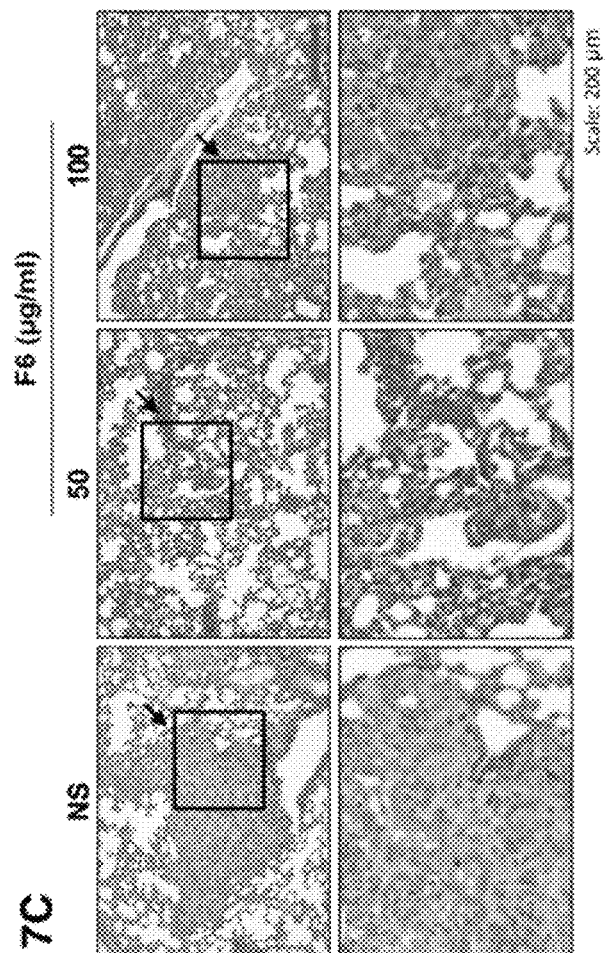

After understanding the tumor suppression potency of our formulated pre-miR-302 drug (F6) on different human lung cancer cell types, we further analyzed its in-vivo therapeutic potency using an orthotopic lung cancer mouse model. FIGS. 16A and 16B showed the time schedule flowchart of F6 treatment frequency and image taking frequency used in an in-vivo bio-imaging system (IVIS). For orthotopic tumor implantation assays, A549-Luci lung cancer cells ($1*10^5$ cells in 20 µl PBS containing 10 ng Matrigel) were injected into the pleural cavity of 6-week-old NOD SCID mice (n=9 in treatment groups and n=3 in control group). A bio-imaging study with luciferase image observation indicated that these implanted mice developed many lung metastasis nodules four (4) weeks after implantation. After that, mice were treated with F6 twice per week via tail vein injection until sacrifice (FIG. 17A). On day-14 post-implantation, mice were divided into three groups: normal saline (NS), and treatments of either 50 or 100 µg/mL of F6, as shown in the imaging results of IVIS (FIG. 17B). The volume of F6 solution used was calculated based on the ratio of body weight and total blood volume in order to keep the same F6 concentration treated in the same group of tested mice. Luciferase signals were observed and measured once per week. In the end, mice were sacrificed 42 days after the first F6 treatment. Major organs such as lung, live, spleen, and kidneys were collected and fixed by 10% formalin, and then the resulting lung nodules were counted using gross and microscopic examination. The number of mice used for the experiments was based on the goal of having 98% power to detect a 2-fold between-group difference in nodule number at $P<0.05$.

Figure 19B:
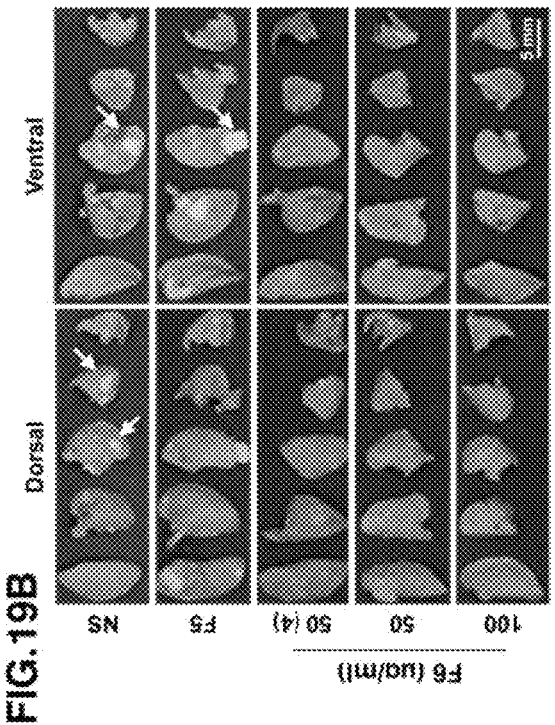
FIGS. 19A, 19B and 19C show the therapeutic results of the second animal trial experiments with a reduced frequency of drug treatments compared to that of the first animal trial, using a formulated pre-miR-302 (F6) drug, to treat highly malignant and metastatic human NSCLC in mice.
Figure 19A:
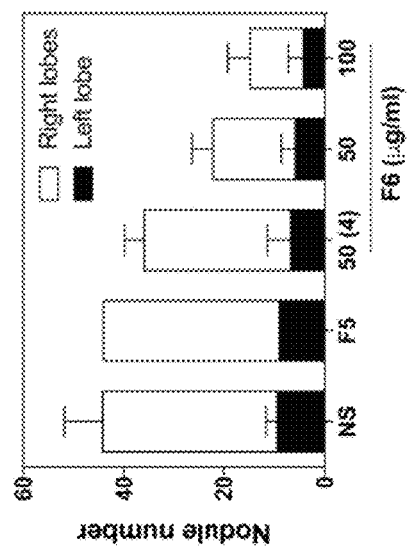
Figure 19C:
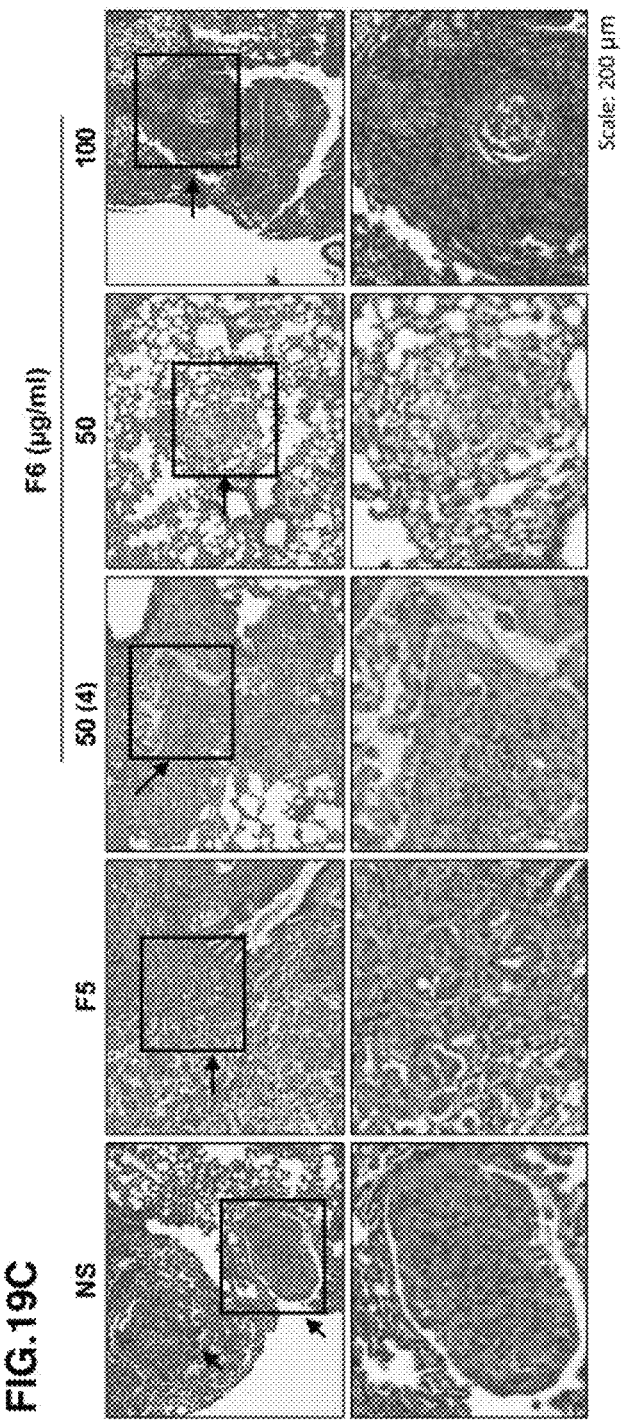

In animal trials using in-vivo orthotopic lung cancer assays (FIGS. 18A-18C), we injected lung cancer cells in the left pleural cavity of each tested mouse to observe the lung to lung metastases. As a result, the cancer nodules found in the right lobes indicated the metastasis of lung cancers from the primary cancer implant side in the left lobe. FIG. 18A demonstrated the numbers of lung cancer nodules in different experimental and control groups, and FIG. 18B showed the representative photo pictures. In FIG. 18A, the black bar illustrated the nodules found in left lobe, and the white bar showed the nodules found in right lobes. As a result shown in FIGS. 18A and 18B, the nodule numbers in both treatment groups (50 and 100 µg/ml) were significantly decreased in both left and right lobes of lung. Further histological examination (FIG. 18C) was also performed to observe typical lung adenocarcinoma structures (circled and pointed by a black arrow) in all groups In order to further evaluate the strong therapeutic effects of the F6 drug on metastatic lung adenocarcinoma, we reduced the treatment frequency of F6 solution in the in-vivo orthotopic lung cancer model (n=11 for both treatment groups and n=5 for control group). As shown in FIGS. 19A and 19B, in this repeated animal trials, mice were treated with F6 via tail vein injection twice per week during the week 3 and 4 and then once a week after week 5 until sacrifice. The applied dosage of F6 was calculated based on the ratio of body weight and total blood volume in order to keep the same F6 concentration treated in all tested mice. Luciferase signals were observed and measured once per week. In the end, mice were sacrificed on day-42 post-treatment. To assess the acute toxicity effects of the pre-miR-302 drug, the mice of one tested group were treated only four times of F6 during the week 3 and 4, which was labeled as the 50 (4) group (FIG. 19B). Furthermore, we also tested the toxicity of glycylglycerin only formula in this in-vivo mouse model to rule out any possible toxicity interference of the delivery formulation agent (F5), which actually presented neither toxicity nor any significant effect on the cancer cells.

9. Statistic Analysis

Any change over 75% of signal intensity in the analyses of immunostaining, western blotting and northern blotting was considered as a positive result, which in turn is analyzed and presented as mean±SE. Statistical analysis of data was performed by one-way ANOVA. When main effects were significant, the Dunnett's post-hoc test was used to identify the groups that differed significantly from the controls. For pairwise comparison between two treatment groups, the two-tailed student t test was used. For experiments involving more than two treatment groups, ANOVA was performed followed by a post-hoc multiple range test. Probability values of $p<0.05$ was considered significant. All p values were determined from two-tailed tests.

REFERENCES

1. Immordino M L, Dosio F, Cattel L. (2006) Int J Nanomedicine. Stealth liposomes: review of the basic science, rationale, and clinical applications, existing and potential. *Int J Nanomedicine* 1, 297-315.
2. WIPO Patent No. WO2011143237 to Meyering.
3. Pereira G R, Collett J H, Garcia S B, Thomazini J A, Bentley MVLB. (2002) Glycerol monooleate/solvents systems for progesterone transdermal delivery: in vitro permeation and microscopic studies. *Brazilian Journal of Pharmaceutical Sciences* 38, 55-62.
4. Zhen G, Hinton T M, Muir B W, Shi S, Tizard M, McLean K M, Hartley P G, Gunatillake P. (2012) Glycerol monooleate-based nanocarriers for siRNA delivery in vitro. *Mol Pharm.* 9, 2450-2457.
5. Gao H, Elsabahy M, Giger E V, Li D, Prud'homme R E, Leroux J C. (2010) Aminated linear and star-shape poly (glycerol methacrylate)s: synthesis and self-assembling properties. *Biomacromolecules*. 11, 889-895.
6. Gao H, Lu X, Ma Y, Yang Y, Li J, Wu G, Wang Y, Fan Y, Ma J. (2011) Amino poly(glycerol methacrylate)s for oligonucleic acid delivery with enhanced transfection efficiency and low cytotoxicity. *Soft Matter* 7, 9239-9247.
7. European Patent Application No. EP92116370.5 to Nair.
8. WIPO Patent No. WO2009029046 to Kim.
9. U.S. Pat. No. 5,618,933 to Dordick.
10. Banerjee G, Nandi G, Mahato S B, Pakrashi A, Basu M K. (1996) Drug delivery system: targeting of pentamidines to specific sites using sugar grafted liposomes. *Journal of Antimicrobial Chemotherapy* 38, 145-150.
11. WIPO Patent No. WO 2002032398 to Kohane.
12. Davis B G and Robinson M K. (2002) Drug delivery systems based on sugar-macromolecule conjugates. *Current Opinion in Drug Discovery & Development* 5, 279-288.
13. Blanchfield J and Toth I. (2004) Lipid, sugar and liposaccharide based delivery systems 2. *Current Medicinal Chemistry* 11, 2375-2382.
14. Morris G A, Kok M S, Harding S E, Adams G G. (2010) Polysaccharide drug delivery systems based on pectin and chitosan. *Biotechnology and Genetic Engineering Reviews* 27, 257-284.
15. Cuña M, Alonso-Sandel M, Remuñán-López C, Pivel J P, Alonso-Lebrero J L, Alonso M J. (2006) Development of phosphorylated glucomannan-coated chitosan nanoparticles as nanocarriers for protein delivery. *J Nanosci Nanotechnol.* 6, 2887-2895.
16. Graf A, Ablinger E, Peters S, Zimmer A, Hook S, Rades T. (2008) Microemulsions containing lecithin and sugar-based surfactants: nanoparticle templates for delivery of proteins and peptides. *Int J Pharm.* 350, 351-360.
17. Davis M E, Zuckerman J E, Choi C H, Seligson D, Tolcher A, Alabi C A, Yen Y, Heidel J D, Ribas A. (2010) Evidence of RNAi in humans from systemically administered siRNA via targeted nanoparticles. *Nature* 464, 1067-1070.
18. Bhatia S, Mohr A, Mathur D, Parmar V S, Haag R, Prasad A K. (2011) Biocatalytic route to sugar-PEG-based polymers for drug delivery applications. *Biomacromolecules* 12, 3487-3498.
19. Ellis G A, Palte M J, Taines R T. (2012) Boronate-Mediated Biologic Delivery. *Journal of American Chemical Society* 134, 3631-3634.
20. Lin S L, Jiang A, Chang D, and Ying S Y. (2008) Loss of mir-146a function in hormone-refractory prostate cancer. *RNA* 14, 417-424.
21. Lin S L, Chang D, Chang-Lin S, Lin C H, Wu D T S, Chen D T, and Ying S Y. (2008) Mir-302 reprograms human skin cancer cells into a pluripotent E S-cell-like state. *RNA* 14, 2115-2124.
22. Lin S L, Chang D, Ying S Y, Leu D, and Wu D T S. (2010) MicroRNA miR-302 inhibits the tumorigenecity of human pluripotent stem cells by coordinate suppression of CDK2 and CDK4/6 cell cycle pathways. *Cancer Res.* 70, 9473-9482.
23. U.S. Pat. No. 9,387,251 to Lin.
24. Chang-Lin S, Hung A, Chang D C, Lin Y W, Ying S Y, Lin S L. (2016) Novel glycylated sugar alcohols protect ESC-specific microRNAs from degradation in iPS cells. *Nucleic Acids Res.* 44, 4894-4906.
25. Lin S L. (2018) Identification and Isolation of Novel Sugar-Like RNA Protecting Materials: Glycylglycerins from Pluripotent Stem Cells. *Methods Mol Biol.* 1733, 305-316.

| SEQUENCE LISTING |
| --- |

(1) GENERAL INFORMATION:
   (iii) NUMBER OF SEQUENCES: 5

(2) INFORMATION FOR SEQ ID NO: 1:
   (i) SEQUENCE CHARACTERISTICS:
      (A) LENGTH: 23 base pairs
      (B) TYPE: nucleic acid
      (C) STRANDEDNESS: duplex
      (D) TOPOLOGY: siRNA

```
                          SEQUENCE LISTING
```

```
       (ii) MOLECULE TYPE: RNA
            (A) DESCRIPTION: /desc = "synthetic"
       (iii) HYPOTHETICAL: YES
       (iv) ANTI-SENSE: YES
       (xi) SEQUENCE DESCRIPTION: SEQ ID NO: 1:
  GUUGGUUGCC AUAACAAGUG UGC                                     23

(2) INFORMATION FOR SEQ ID NO: 2:
       (i) SEQUENCE CHARACTERISTICS:
            (A) LENGTH: 23 base pairs
            (B) TYPE: nucleic acid
            (C) STRANDEDNESS: duplex
            (D) TOPOLOGY: siRNA
       (ii) MOLECULE TYPE: RNA
            (A) DESCRIPTION: /desc = "synthetic"
       (iii) HYPOTHETICAL: YES
       (iv) ANTI-SENSE: YES
       (xi) SEQUENCE DESCRIPTION: SEQ ID NO: 2:
  GAUAAAGGAG UUGCACCAGG UAC                                     23

(2) INFORMATION FOR SEQ ID NO: 3:
       (i) SEQUENCE CHARACTERISTICS:
            (A) LENGTH: 23 base pairs
            (B) TYPE: nucleic acid
            (C) STRANDEDNESS: duplex
            (D) TOPOLOGY: siRNA
       (ii) MOLECULE TYPE: RNA
            (A) DESCRIPTION: /desc = "synthetic"
       (iii) HYPOTHETICAL: YES
       (iv) ANTI-SENSE: YES
       (xi) SEQUENCE DESCRIPTION: SEQ ID NO: 3:
  CUACCGAAGA GCUACCAGAC GAA                                     23

(2) INFORMATION FOR SEQ ID NO: 4:
       (i) SEQUENCE CHARACTERISTICS:
            (A) LENGTH: 23 base pairs
            (B) TYPE: nucleic acid
            (C) STRANDEDNESS: single
            (D) TOPOLOGY:
       (ii) MOLECULE TYPE: RNA
            (A) DESCRIPTION: /desc = "synthetic"
       (iii) HYPOTHETICAL: YES
       (iv) ANTI-SENSE: NO
       (xi) SEQUENCE DESCRIPTION: SEQ ID NO: 4:
  UAAGUGCUUC CAUGUUUUAG UGU                                     23

(2) INFORMATION FOR SEQ ID NO: 5:
       (i) SEQUENCE CHARACTERISTICS:
            (A) LENGTH: 23 base pairs
            (B) TYPE: nucleic acid
            (C) STRANDEDNESS: single
            (D) TOPOLOGY:
       (ii) MOLECULE TYPE: RNA
            (A) DESCRIPTION: /desc = "synthetic"
       (iii) HYPOTHETICAL: YES
       (iv) ANTI-SENSE: YES
       (xi) SEQUENCE DESCRIPTION: SEQ ID NO: 5:
  ACACUAAAAC AUGGAAGCAC UUA                                     23
```

```
                          SEQUENCE LISTING

<160> NUMBER OF SEQ ID NOS: 5

<210> SEQ ID NO 1
<211> LENGTH: 23
<212> TYPE: RNA
<213> ORGANISM: Artificial Sequence
<220> FEATURE:
<223> OTHER INFORMATION: Synthetic RNA

<400> SEQUENCE: 1
guugguugcc auaacaagug ugc                                       23

<210> SEQ ID NO 2
<211> LENGTH: 23
<212> TYPE: RNA
<213> ORGANISM: Artificial Sequence
<220> FEATURE:
<223> OTHER INFORMATION: Synthetic RNA

<400> SEQUENCE: 2
gauaaaggag uugcaccagg uac                                       23

<210> SEQ ID NO 3
<211> LENGTH: 23
<212> TYPE: RNA
<213> ORGANISM: Artificial Sequence
<220> FEATURE:
<223> OTHER INFORMATION: Synthetic RNA

<400> SEQUENCE: 3
cuaccgaaga gcuaccagac gaa                                       23

<210> SEQ ID NO 4
<211> LENGTH: 23
```

```
<212> TYPE: RNA
<213> ORGANISM: Artificial Sequence
<220> FEATURE:
<223> OTHER INFORMATION: Synthetic RNA
<220> FEATURE:
<221> NAME/KEY: modified_base
<222> LOCATION: (1)..(1)
<223> OTHER INFORMATION: Cy5.5 label

<400> SEQUENCE: 4
uaagugcuuc cauguuuuag ugu                                              23

<210> SEQ ID NO 5
<211> LENGTH: 23
<212> TYPE: RNA
<213> ORGANISM: Artificial Sequence
<220> FEATURE:
<223> OTHER INFORMATION: Synthetic RNA
<220> FEATURE:
<221> NAME/KEY: modified_base
<222> LOCATION: (1)..(1)
<223> OTHER INFORMATION: Cy5.5 label

<400> SEQUENCE: 5
acacuaaaac auggaagcac uua                                              23
```

The invention claimed is:

1. A composition for formulating nucleic acid compositions with sugars and sugar alcohols into stable complexes for in-vitro, ex vivo and in-vivo delivery into mammalian cells, comprising:
   (a) at least a nucleic acid composition with at least a negative charge; and
   (b) at least a sugar or sugar alcohol composition modified by trimethylglycylation,
   wherein (a) and (b) are mixed together under a condition to form at least a delivery complex, wherein said delivery complex is delivered into mammalian cells via acetylcholine receptors.

2. The composition as defined in claim 1, wherein said nucleic acid composition is small hairpin RNAs.

3. The composition as defined in claim 1, wherein said sugar or sugar alcohol composition is glycerin (glycerol).

4. The composition as defined in claim 1, wherein said trimethylglycylation is a chemical reaction that replaces the hydroxyl (HO—) groups of a sugar alcohol or sugar with betaine's trimethylglycyl [$(CH_3)_3N^+CH_2COO$—] groups and thus results in the formation of an ether (R—O—R) linkage between each OH-removed carbon of the sugar/sugar alcohol and the trimethylglycyl group.

5. The composition as defined in claim 1, wherein said sugar or sugar alcohol composition after modified by trimethylglycylation forms mono-trimethylglycylglycerins (mono-TMGG; $C_8H_{18}O_4N_1$ MW=190~193g/mole), di-trimethylglycylglycerin (di-TMGG; $C_{13}H_{28}O_5N_2$ MW=290~293g/mole), and/or tri-trimethylglycylglycerin (tri-TMGG; $C_{18}H_{38}O_6N_3$ MW=390~393 g/mole).

6. The composition as defined in claim 1, wherein said sugar or sugar alcohol composition is capable of protecting said nucleic acid compositions from degradation.

7. The composition as defined in claim 1, wherein said sugar or sugar alcohol composition is capable of enhancing the delivery efficiency of said nucleic acid compositions into mammalian cells via acetylcholine receptors in vitro, ex vivo and in vivo.

8. The composition as defined in claim 1, wherein said condition is incubation at a temperature equal or larger than 75° C. and at a pressure equal or higher than 100 kPa.

9. The composition as defined in claim 8, wherein said condition is incubation at a temperature about 100° C. to 160° C. and at a pressure about 101 to 250 kPa.

10. The composition as defined in claim 1, wherein said delivery complex is formed by the ionic or electrostatic affinity occurring between the modified sugar or sugar alcohol and the nucleic acid composition.

11. The composition as defined in claim 1, wherein said delivery complex is useful for therapeutic applications.

12. The composition as defined in claim 1, wherein said modified sugar or sugar alcohol is capable of forming trimethylglycyl-glycylglycerin mixtures.

13. The composition as defined in claim 1, wherein said modified sugar or sugar alcohol is capable of forming polymers with glycylglycerins and amino acids.

14. The composition as defined in claim 1, wherein said modified sugar or sugar alcohol contains at least a trimethylglycyl [$(CH_3)_3N^+CH_2COO$—] group that structurally resembles acetylcholine.

15. The composition as defined in claim 1, wherein said modified sugar or sugar alcohol is capable of interacting with acetylcholine receptors.

16. The composition as defined in claim 1, wherein said modified sugar or sugar alcohol is capable of being used to replace acetylcholine to stimulate or inhibit acetylcholine receptors.

17. The composition as defined in claim 1, wherein said modified sugar or sugar alcohol is useful for developing therapeutic applications and devices.

18. The composition as defined in claim 1, wherein said modified sugar or sugar alcohol is useful for formulating nucleic acid-based compositions into medicine drugs.

19. The composition as defined in claim 1, wherein said modified sugar or sugar alcohol is useful for formulating nucleic acid-based medicines for treating respiratory diseases and infections.

20. The composition as defined in claim 1, wherein said modified sugar or sugar alcohol is useful for formulating small hairpin RNAs into vaccines for treating viral infection.

21. The composition as defined in claim 20, wherein said formulated small hairpin RNAs vaccines induce RNAi effects.

22. The composition as defined in claim 1, wherein said nucleic acid composition induce immune responses to generate antibodies directed against viruses.

23. The composition as defined in claim 22, wherein said viruses are RNA viruses.

* * * * *